US009861682B2

(12) United States Patent
Jorgensen et al.

(10) Patent No.: US 9,861,682 B2
(45) Date of Patent: *Jan. 9, 2018

(54) TREATMENT OF HYPERALGESIA, SPONTANEOUS PAIN, AND PHANTOM PAIN

(71) Applicant: HOBA Therapeutics ApS, Copenhagen (DK)

(72) Inventors: Jesper Roland Jorgensen, Frederiksberg (DK); Lars Ulrik Wahlberg, Tiverton, RI (US); Teit E. Johansen, Hørsholm (DK)

(73) Assignee: HOBA THERAPEUTICS APS, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/277,698

(22) Filed: Sep. 27, 2016

(65) Prior Publication Data

US 2017/0143794 A1   May 25, 2017

Related U.S. Application Data

(63) Continuation of application No. 14/241,568, filed as application No. PCT/DK2012/050330 on Sep. 5, 2012, now Pat. No. 9,474,786.

(60) Provisional application No. 61/531,024, filed on Sep. 5, 2011.

(51) Int. Cl.
| | |
|---|---|
| A61K 38/00 | (2006.01) |
| A61K 38/16 | (2006.01) |
| A61K 38/17 | (2006.01) |
| A61K 38/18 | (2006.01) |
| C07K 14/00 | (2006.01) |
| C07K 14/475 | (2006.01) |
| A61K 9/00 | (2006.01) |

(52) U.S. Cl.
CPC .......... *A61K 38/185* (2013.01); *A61K 9/0085* (2013.01)

(58) Field of Classification Search
None
See application file for complete search history.

(56) References Cited

U.S. PATENT DOCUMENTS

| | | | |
|---|---|---|---|
| 4,407,957 | A | 10/1983 | Lim |
| 5,219,990 | A | 6/1993 | Androphy et al. |
| 5,798,113 | A | 8/1998 | Dionne et al. |
| 5,800,828 | A | 9/1998 | Dionne et al. |
| 5,981,277 | A | 11/1999 | Fransen et al. |
| 8,334,264 | B2 | 12/2012 | Jorgensen et al. |
| 8,404,642 | B2 | 3/2013 | Jorgensen et al. |
| 2007/0275026 | A1 | 11/2007 | Gronborg et al. |
| 2012/0184492 | A1 | 7/2012 | Gronborg et al. |
| 2013/0267464 | A1 | 10/2013 | Jorgensen et al. |
| 2013/0303459 | A1 | 11/2013 | Jorgensen et al. |

FOREIGN PATENT DOCUMENTS

| | | |
|---|---|---|
| WO | WO 1992/019195 | 11/1992 |
| WO | WO 1993/022437 | 11/1993 |
| WO | WO 1995/005452 | 2/1995 |
| WO | WO 1997/034586 | 9/1997 |
| WO | WO 1997/044065 | 11/1997 |
| WO | WO 2001/025427 | 4/2001 |
| WO | WO 2001/039786 | 6/2001 |
| WO | WO 2001/054474 | 8/2001 |
| WO | WO 2001/055301 | 8/2001 |
| WO | WO 2001/055440 | 8/2001 |
| WO | WO 2001/057190 | 8/2001 |
| WO | WO 2001/083510 | 11/2001 |
| WO | WO 2002/078730 | 10/2002 |
| WO | WO 2003/066877 | 8/2003 |
| WO | WO 2004/035732 | 4/2004 |
| WO | WO 2004/079014 | 9/2004 |
| WO | WO 2005/095450 | 10/2005 |
| WO | WO 2006/110593 | 10/2006 |
| WO | WO 2007/100898 | 7/2007 |
| WO | WO 2010/009732 | 1/2010 |
| WO | WO 2012/041328 | 4/2012 |

OTHER PUBLICATIONS

International Search Report in International Application No. PCT/DK2009/050165, dated Jul. 12, 2009 , 8 pages.
Written Opinion in International Application No. PCT/DK2009/050165, dated Jul. 12, 2009, 5 pages.
International Search Report in International Application No. PCT/DK2012/050330, dated Dec. 12, 2012, 11 pages.
International Preliminary Report on Patentability in International Application No. PCT/DK2012/050330, dated Dec. 8, 2013, 7 pages.
Anderson et al., "Ciliary neurotrophic factor protects striatal output neurons in an animal model of Huntington disease," Proc. Natl. Acad. Sci. USA, Jul. 1996, 93:7346-7351.
Colton, "Engineering Challenges in Cell-Encapsulation Technology," Trends Biotechnol., May 1996, 14(5):158-162.
Fransen et al., "Molecular cloning of a novel macrophage-derived cytokine (SMAF-1) and its immunomodulating capacities." Cytokine, Nov. 1999, 11(11):975, abstract 254, Seventh Annual Conference of the International Cytokine Society; Hilton Head, South Carolina, USA; Dec. 5-9, 1999 ISSN: 1043-4666.
Fransson et al., "A Novel Neurotrophic Factor Supports Spiral Ganglion Neuron Survival and Their Electrical Responsiveness In Vivo," Karolinska Institutet, NsGene NS, Poster, 2010, ANS/AuPS 2010 Joint Meeting, Sydney, Australia, 1 page.
GenBank Accession No. AAH00662, Nov. 29, 2000, 2 pages.
GenBank Accession No. AAH37181, Sep. 23, 2002, 2 pages.
GenBank Accession No. AAH88383, Dec. 22, 2004, 2 pages.
GenBank Accession No. AAK61247, Jun. 8, 2001, 2 pages.
GenBank Accession No. AAM78739, Nov. 6, 2001, 1 page.

(Continued)

*Primary Examiner* — Christine J Saoud
*Assistant Examiner* — Jon M Lockard
(74) *Attorney, Agent, or Firm* — Dinsmore & Shohl LLP

(57) ABSTRACT

The present invention relates to use of Cometin in a method of treatment of allodynia, hyperalgesia, spontaneous pain and/or phantom pain. In a preferred embodiment the disorder to be treated is thermal allodynia and thermal hyperalgesia. The Cometin polypeptide may be delivered as a polypeptide or by administration of an expression vector for expression of Cometin, a cell line transformed or transduced with said vector and a capsule comprising said cells.

14 Claims, 6 Drawing Sheets

(56) References Cited

OTHER PUBLICATIONS

GenBank Accession No. AAM79723, Nov. 6, 2001, 1 page.
GenBank Accession No. ABA06589, Jan. 10, 2002, 3 pages.
GenBank Accession No. ABA06759, Jan. 10, 2002, 3 pages.
GenBank Accession No. ABB10367, Jan. 10, 2002, 3 pages.
GenBank Accession No. ABB10537, Jan. 10, 2002, 3 pages.
GenBank Accession No. ABB57447, Mar. 15, 2002, 1 page.
GenBank Accession No. ADP29324, Aug. 12, 2004, 2 pages.
GenBank Accession No. BG806341, Dec. 21, 2001, 1 page.
GenBank Accession No. CAB56188, Sep. 17, 1999, 2 pages.
GenBank Accession No. NP_076947, Feb. 27, 2001, 2 pages.
Gong et al., "Metrnl: A New Secreted Protein Inhibit Differentiation of MG-63," J Bone and Mineral Res., 2007, 22(Suppl 1):S142, 1 page.
Grønborg et al., "Identification of Secreted Neurotrophic Factors Using Bioinformatics Combined with Expression Analysis," Program No. 825.2, Abstract Viewer/Itinerary Planner, Washington, DC: Society for Neuroscience, 2005, Abstract Only, 1 page.
Haughey et al., "Disruption of neurogenesis in the subventricular zone of adult mice, and in human cortical neuronal precursor cells in culture, by amyloid beta-peptide: implications for the pathogenesis of Alzheimer's disease," Neuromolecular Med., 2002, 1(2):125-35 (Abstract Only).
Jackowski, "Neural Injury Repair: Hope for the Future as Barriers to Effective CNS Regeneration Become Clearer," Br J Neurosurgery, 1995, 9:303-317.
Jørgensen et al., "Characterization of Meteorin—An Evolutionary Conserved Neurotrophic Factor," J. Mol. Neurosci., 2009, 13 pages.
Jørgensen et al., "Cometin is a novel neurotrophic factor that promotes neurite outgrowth and neuroblast migration in vitro and supports survival of spiral ganglion neurons in vivio," Experimental Neurology, 2012, 233:172-181.
Jørgensen et al., "Lentiviral Delivery of Meteorin Protects Striatal Neurons Against Excitotoxicity and Reverses Motor Deficits in the Quinolinic Acid Rat Model," Neurobiol Dis., doi:10:10.1016/j.nbd.2010.09.003, 2010, 9 pages.
Jørgensen et al., "Meteorin reverses hypersensitivity in rat models of neuropathic pain," Experimental Neurol., 2012, 237:260-266.
Jørgensen et al., "Poster 323.8: Meteorin and Meteorin-Like Initial Characterization of a Novel Growth Factor Family," Presented at SfN Meeting, 2008, 1 page.
Jørgensen et al., Poster: "Meteorin Protects Striatal Neurons and Improves Behavior in a Rat Model of Huntington's Disease," Jan. 28, 2010, 1 page.
Lim et al., "The adult neural stem cell niche: lessons for future neural cell replacement strategies," Neurosurg Clin N Am., Jan. 2007, 18(1):81-92 (Abstract Only).
Matheson et al., "Glial Cell Line-Derived Neurotrophic Factor (GDNF) is a Neurotrophic Factor for Sensory Neurons: Comparison with the Effects of the Neurotrophins," J Neurobiol., 1997, 32(1):22-32.
Mizuno et al., "Brain-Derived Neurotrophic Factor Promotes Differentiation of Striatal GABAergic Neurons," Dev Biol., 1994, 165(1):243-256 (Abstract Only).
Mu et al., "Gene Expression in the Developing Mouse Retina by EST Sequencing and Microarray Analysis," Nucl. Acids Res., 2001, 24:4983-4993.
Navarro-Galvel et al., "HNSG33 Effects on Survival and Differentiation of Human Neural Stem Cell-Derived Neuronal and Glial Progeny," Program No. 248.14, Abstract Viewer/Itineraty Planner, Washington DC: Society for Neuroscience, 2005, 2 pages.
Nishino et al., "Meteorin: A Secreted Protein that Regulates Glial Cell Differentiation and Promotes Axonal Extension," EMBO J., 2004, 23(9):1998-2008.
Office Action issued in Japanese Application No. 2014-528860, dated Jun. 29, 2016, with English Translation, 6 pages.
Ossipov M., "Growth Factors and Neuropathic Pain," Current Pain and Headache Report, 2011, 15(3):185-192.
Pezet et al., "Neurotrophins: mediators and modulators of pain," Annu Rev Neurosci., 2006, 29:507-38.
Ramialison et al., "Rapid Identification of PAX2/51 Direct Downstream Targets in the Otic Vesical by Combinatorial Use of Bioinformatics Tools," Genome Biol., 2008, 9:R145 (11 pages).
Reagan-Shaw et al., "Dose translation from animal to human studies revisited," FASEB J., 2008, 22:659-661.
Rudinger, in "Peptide Hormones," University Park Press, Ed. Parsons, 1976, pp. 1-7.
Tanaka et al., "Increased Expression of the Neurotrophic Growth Factor Meteorin-Like Protein in Lesional Skin of Individuals with Familial Primary Localized Cutaneous Amyloidosis," Kings College London, 39th Annual Meeting of European Society Dermatological Res., Sep. 9-12, 2009, Budapest, Hungary, Poster, 1 page.
Tattersfield et al., "Neurogenesis in the striatum of the quinolinic acid lesion modle of Huntington's disease," Neuroscience, 2004, 127(2):319-32 (Abstract Only).
Thompson et al., "Clustal W: improving the sensitivity of progressive multiple sequence alignment through sequence weighting, positions-specific gap penalties and weight matrix choice," Nucleic Acids Res, 1994, 22:4673-4680.
Todoroki et al., "Ropivacaine Inhibits Neurite Outgrowth in PC-12 Cells," Anesth. Analg., 2004, 99:828-832.
Ventimiglia et al., "The Neurotrophins BDNF, NT-3 and NT-4/5 Promote Survival and Morphological and Biochemical Differentiation of Striatal Neurons In Vitro," Eur. J. Neurosci., 1995, 7:213-222, Abstract Only, 1 page.
Walker et al., "Application of a Rat Multiple Tissue Gene Expression Data Set," Genome Res., 2004, 14:742-749.
Watanabe, et al., *Shikagaku-hou* (Odontology Report), 2006, 106(6):469-475, in Japanese.

Figure 1

```
hCOMETIN    MRGAARAAWGRAGQPWPRPPAPGPPPPPLPLLLLLLAGLLGGAGAQYSSDRCSWKGSGLT
mCOMETIN    MRGAVWAARRRAGQQWPRSPGPGPGPPPPPPLLLLLLLLLGGASAQYSSDLCSWKGSGLT
rCOMETIN    MRGVVWAARRRAGQQWPRSPGPGPGPPPPPPLLLLLLLLLGGASAQYSSDLCSWKGSGLT
            *    **  *  *  *  *  *  ***   * ** ****** hCOMETIN    HEAHRKEVEQVYLRCAAGAVEWMYPTGALIVNLRPNTFSPARHLTVCIRSFTDSSGANIY
mCOMETIN    REARSKEVEQVYLRCSAGSVEWMYPTGALIVNLRPNTFSPAQNLTVCIKPFRDSSGANIY
rCOMETIN    REAHSKEVEQVYLRCSAGSVEWMYPTGALIVNLRPNTFSPAQNLTVCIKPFRDSSGANIY
               ******   ******************     ***  *  ******** hCOMETIN    LEKTGELRLLVPDGDGRPGRVQCFGLEQGGLFVEATPQQDIGRRTTGFQYELVRRHRASD
mCOMETIN    LEKTGELRLLVRDIRGEPGQVQCFSLEQGGLFVEATPQQDISRRTTGFQYELMSGQRGLD
rCOMETIN    LEKTGELRLLVRDVRGEPGQVQCFSLEQGGLFVEATPQQDISRRTTGFQYELMSGQRGLD
            ***********  *  *    *************  ********     *  * hCOMETIN    LHELSAPCRPCSDTEVLLAVCTSDFAVRGSIQQVTHEPERQDSAIHLRVSRLYRQKSRVF
mCOMETIN    LHVLSAPCRPCSDTEVLLAICTSDFVVRGFIEDVTHVPEQQVSVIYLRVNRLHRQKSRVF
rCOMETIN    LHVLSAPCRPCSDTEVLLAICTSDFVVRGFIEDVTHVPEQQVSVIHLRVSRLHRQKSRVF
             ************ * *  *   ***  *  *  *  *  ******* hCOMETIN    EPVPEGDGHWQGRVRTLLECGVRPGHGDFLFTGHMHFGEARLGCAPRFKDFQRMYRDAQE
mCOMETIN    QPAPEDSGHWLGHVTTLLQCGVRPGHGEFLFTGHVHFGEAQLGCAPRFSDFQRMYRKAEE
rCOMETIN    QPAPEDSGHWLGHVTTLLQCGVRPGHGEFLFTGHVHFGEAQLGCAPRFSDFQKMYRKAEE
            *     *  *  *  *  ***  **  *  ***  *  ***  *  * hCOMETIN    RGLNPCEVGTD
mCOMETIN    MGINPCEINME
rCOMETIN    RGINPCEINME
              *  ****
```

Figure 2

```
hCOMETIN   MRGAARAAWGRAGQPWPRPPAPGPPPPPLPLLLLLLAGLLGG-AG-AQYSSDRCSWKGSG
mCOMETIN   MRGAVWAARRRAGQQWPRSPGPGPGPPPPPPLLLLLLLLLGG-AS-AQYSSDLCSWKGSG
rCOMETIN   MRGVVWAARRRAGQQWPRSPGPGPGPPPPPPLLLLLLLLLGG-AS-AQYSSDLCSWKGSG
hMETRN     -MGFPAAA-----------------------LLCALCCGLLAP-AARAGYSEERCSWRGSG
mMETRN     MLVAT-------------------------LLCALCCGLLAASAH-AGYSEDRCSWRGSG
rMETRN     MLVAA-------------------------LLCALCCGLLAASAR-AGYSEDRCSWRGSG
                                                           *   *   ** *   *      * *** hCOMETIN   LTHEAHRKEVEQVYLRCAAGAVEWMYPTGALIVNLR---PNTFSPARHLTVCIRSFTDSS
mCOMETIN   LTREARSKEVEQVYLRCSAGSVEWMYPTGALIVNLR---PNTFSPAQNLTVCIKPFRDSS
rCOMETIN   LTREAHSKEVEQVYLRCSAGSVEWMYPTGALIVNLR---PNTFSPAQNLTVCIKPFRDSS
hMETRN     LTQEP--GSVGQLALACAEGAVEWLYPAGALRLTLGGPDPRA----RPGIACLRPVRPFA
mMETRN     LTQEP--GSVGQLTLDCTEGAIEWLYPAGALRLTLGGPDPGT----RPSIVCLRPERPFA
rMETRN     LTQEP--GSVGQLTLDCTEGAIEWLYPAGALRLTLGGSDPGT----RPSIVCLRPTRPFA
           ** *      *  *  *   *    ***    *    * hCOMETIN   GANIYLEK-TG-ELRLLVPDGDGRPGRVQC--FG-LEQGGLFVEATPQQDIGRRTTGFQY
mCOMETIN   GANIYLEK-TG-ELRLLVRDIRGEPGQVQC--FS-LEQGGLFVEATPQQDISRRTTGFQY
rCOMETIN   GANIYLEK-TG-ELRLLVRDVRGEPGQVQC--FS-LEQGGLFVEATPQQDISRRTTGFQY
hMETRN     GAQVFAER-AGGALELLLAEGPGPAGG-RCVRWGPRERRALFLQATPHQDISRRVAAFRF
mMETRN     GAQVFAERMTG-NLELLLAEGPDLAGG-RCMRWGPRERRALFLQATPHRDISRRVAAFRF
rMETRN     GAQVFAERMAG-NLELLLAEGQGLAGG-RCMRWGPRERRALFLQATPHRDISRRVAAFQF
           **       *    *  *  **    *     *    *   *      * hCOMETIN   ELVRRHRAS---DLHE-----LSAP--CRPCSDTEVLLAVCTSDFAVRGSIQQVTHEPER
mCOMETIN   ELMSGQRGL---DLHV-----LSAP--CRPCSDTEVLLAICTSDFVVRGFIEDVTHVPEQ
rCOMETIN   ELMSGQRGL---DLHV-----LSAP--CRPCSDTEVLLAICTSDFVVRGFIEDVTHVPEQ
hMETRN     ELREDGRPELPPQAHG-----LGVDGACRPCSDAELLLAACTSDFVIHGIIHGVTHDVEL
mMETRN     ELHEDQRAE---MSPQAQGLGVDGA--CRPCSDAELLLAACTSDFVIHGTIHGVAHDTEL
rMETRN     ELHEDQRAE---MSPQAQGFGVDGA--CRPCSDAELLLTACTSDFVIHGTIHGVVHDMEL
           **       *                  ***** *    **    *   *   * hCOMETIN   QDSAIHLRVSRLYRQKSRVFEPVPEG--DGHWQG--R--VRTLLECGVRPGHGDFLFTGH
mCOMETIN   QVSVIYLRVNRLHRQKSRVFQPAPED--SGHWLG--H--VTTLLQCGVRPGHGEFLFTGH
rCOMETIN   QVSVIHLRVSRLHRQKSRVFQPAPED--SGHWLG--H--VTTLLQCGVRPGHGEFLFTGH
hMETRN     QESVITVVAARVLRQTPPLFQAGRSG--D---QGLTS--IRTPLRCGVHPGPGTFLFMGW
mMETRN     QESVITVVVARVIRQTLPLFK---EG--SSEGQG--RASIRTLLRCGVRPGPGSFLFMGW
rMETRN     QESVITVVATRVIRQTLPLFQ---EGSSEGRGQA--S--VRTLLRCGVRPGPGSFLFMGW
           * *            *  **    *                     *  *  *  *  *** * hCOMETIN   MHFGEARLGCAPRFKDFQRMYRDAQERGLNPCEVGTD
mCOMETIN   VHFGEAQLGCAPRFSDFQRMYRKAEEMGINPCEINME
rCOMETIN   VHFGEAQLGCAPRFSDFQKMYRKAEERGINPCEINME
hMETRN     SRFGEARLGCAPRFQEFRRAYEAARAAHLHPCEVALH
mMETRN     SRFGEAWLGCAPRFQEFSRVYSAALTTHLNPCEMALD
rMETRN     SRFGEAWLGCAPRFQEFSRVYSAALAAHLNPCEVALD
           ****  ** ****   *    *     *    ***
```

Figure 3

```
Human      1  -MRGAARAAWGRAGQPWPRPPAPGPPPPPLPLLLLLLAGLLG-GAGA
Cow        1  -MRGATRAAGGRAGQLWPRPPAPGPGPPP---LLLLLAVLLG-GAGA
Mouse      1  -MRGAVWAARRRAGQQWPRSPGPGPGPPPPPPLLLLLLLLLG-GASA
Rat        1  -MRGVVWAARRRAGQQWPRSPGPGPGPPPPPPLLLLLLLLLG-GASA
Chicken    1  -MRSA---------------PAAGL----LPLLLGLRLLLGG-GAEA
Xenopus    1  MLRRV-------------------------LLSFFMVILMDRGTSQ
Zebrafish  1  ------------------------MLSPFLAYLLSVVLLCR-IARS Human     49  SDRCSWKGSGLTHEAHRKEVEQVYLRAAGAVEWMYPTGALIVNLRPNTF
Cow       46  SDLCSWKGSGLTHEAHRKEVEQVYLRSAGTVEWMYPTGALIVNLRPNTF
Mouse     49  SDLCSWKGSGLTREARSKEVEQVYLRSAGSVEWMYPTGALIVNLRPNTF
Rat       49  SDLCSWKGSGLTREAHSKEVEQVYLRSAGSVEWMYPTGALIVNLRPNTF
Chicken   30  SDLCNWKGSGLTHESHKKDVEQVYLRSEGSIEWMYPTGALIVNLRPNT-
Xenopus   25  SDMCNWKGSGLTHEGHTKDVEQVYLRSEGSVEWLYPTGAMIINLRPNTL
Zebrafish 25  SDQCSWRGSGLTHEGHTRGVEQVYLRAQGFLEWLYPTGAIVNLRPNTL Human     99  SPA--RHL-TVCIRSFTLSSGANIYLEKTGELRLLVPDGDRPGRVCG
Cow       96  SPS--RNL-TLCIKPLRGSSGANIYLEKTGELKLLVRDGDLGPGQAFG
Mouse     99  SPA--QNL-TVCIKPFRDSSGANIYLEKTGELRLLVRDIRGEPGQVCS
Rat       99  SPA--QNL-TVCIKPFPDSSGANIYLEKTGELRLLVRDVRGEPGQVCS
Chicken   79  SPASYKHL-TVCIKPFKDSAGANIYLEKTGELKLLVRDGERSPSKYCG
Xenopus   75  TSAY-KHL-TVCIKPFKDSKGANIYSEKTGELKLVVPDGENNPHKYLG
Zebrafish 75  SPA--ASLLSVCIKPSKESSGTHLYLDRLGKLRLLLSEGDQAECKVHN Human    146  LEQGGLFVEATPQQDIGRRTTGFQYELVRRERASDLHELSAPCRPSDTE
Cow      143  FEQGGLFVEATPQQDISRRTTGFQYELTSRRTGPDLHALLAPCRPSHTE
Mouse    146  LEQGGLFVEATPQQDISRRTTGFQYELMSGQRGLDLHVLSAPCRPSDTE
Rat      146  LEQGGLFVEATPQQDISRRTTGFQYELMSGQRGLDLHVLSAPCRPSDTE
Chicken  128  YDQGGLFVEATPQQDISRKITGFQYELMSRGIASDLHTVSAPCRPSDTE
Xenopus  123  LDQRGLYIEATPQQDISRKITGFQYELISQRTLSDLHTVSDPCRPSDTE
Zebrafish 123 IQDGALFIEAVPQRDISRKITAFQYELVNHRPGADPQSLSAPCQPTDAE Human    196  VLLAVCSDFAVRGSIQQVTHEPERQDSAIHLRVSRLYRQKSRVFEPVP
Cow      193  VLLAVCSDFVVRGSIQKVTHEPERQESAIHLNVSRLYRQKSRVFRPAP
Mouse    196  VLLAICSDFVVRGFIEDVTHVPEQQVSVIYLRVNRLHRQKSRVFQPAP
Rat      196  VLLAICSDFVVRSFIEDVTHVPEQQVSVIHLRVSRLHRQKSRVFQPAP
Chicken  178  VLLAVCSDFVIRGSIQDVTNEAEEQESVIHVGVNKLYRQKSKVFQLTGE
Xenopus  173  VLLAVCISDFVYKGTIGTVTNDEELQESLIGVTYDKLYRQKSKIE--LRK
Zebrafish 173 VLLAVCSDFVARGRILGVSEEDEQ--TSVTVSLSHLYRQKTQVFVSGGG Human    246  GDGH-WQGRVRTLLECGVRPGHGDELPTGHMHPGEARLGCAPRPKDPQRM
Cow      243  GECGGWRGRVSTLLECGVRPGHGERLPTGHMHPGEAWLGCEPRPKDPQRM
Mouse    246  DSCH-WLGHVTTLLQCGVRPGHGEPLPTGHVHPGEAQLGCAPRPSDPQRM
Rat      246  DSCH-WLGHVTTLLQCGVRPGHGEPLPTGHVHPGEAQLGCAPRPSDPQKM
Chicken  228  S-CN-WRGQIKTLLECGVRPGDGDPLPTGRMHPGEARLGCAPRPKDPQRM
Xenopus  221  ENCG-WECTIRCPRECGVKAGSGSPLPTGRMHPGEPRLGCTPRYSDTRI
Zebrafish 221 RAKR-WTGFVKMSRQCGVKPSDGEPLPTGTVRPGEAWLSCAPRYKDPLRV Human    295  YRDAQERGLNPCVGTD
Cow      293  YRDAEERGLNPCMGTE
Mouse    295  YRKAEEMGINPCINME
Rat      295  YRKAEERGINPCINME
Chicken  276  YKEAKDKGLNPCIGPD
Xenopus  270  YLEAKKQGLNPCISTD
Zebrafish 270 YQDARQQSTNPCHLETD
```

TREATMENT OF HYPERALGESIA, SPONTANEOUS PAIN, AND PHANTOM PAIN

CROSS REFERENCE TO RELATED APPLICATIONS

This application is a continuation of U.S. patent application Ser. No: 14/241,568 filed Apr. 20, 2015 (now U.S. Pat. No: 9,474,786), which is a 35 U.S.C. §371 national phase application of PCT/DK2012/050330 filed Sep. 5, 2012 and which claims priority to U.S. Provisional Application No. 61/531,024 filed Sep. 5, 2011.

FIELD OF INVENTION

The present invention relates to use of Cometin in a method of treatment of allodynia, hyperalgesia, spontaneous pain and/or phantom pain. In a preferred embodiment the disorder to be treated is thermal allodynia and thermal hyperalgesia. The allodynia and/or hyperalgesia are preferably treated in a subject diagnosed with painful diabetic neuropathy, post-herpetic neuralgia or sciatica.

BACKGROUND OF INVENTION

Many therapies have been explored for the treatment of allodynia, hyperalgesia, spontaneous pain and phantom pain with varying degree of success, including non-steroidal anti-inflammatory drugs (NSAIDs), opioids, anticonvulsants, anti-arrhythmics, tricyclic antidepressants and topical agents. Alternative approaches include anaesthetic blocks, epidural administration of steroids and neurosurgical lesions. However, all of the present therapies have modest efficacy in most patients and are palliative rather than curative and their side effects represent significant limitations.

Hence, there is a high unmet need for therapies that treat allodynia, hyperalgesia, spontaneous pain and phantom pain effectively, preferably with only minor side effects not affecting the general health of the patients.

A polypeptide with the sequence of the neurotrophic growth factor Cometin has been described previously in WO 93/22437 (Innogenetics). It is suggested that the protein or its antagonist can be used as antitumor compounds, or anti-inflammatory compounds or as growth activators of T-cells and B-cells, as bone repair compounds as inducer of immunosuppressive cells, as inhibitors of anti-colony stimulating factor; or as trypanocidal agents.

WO 01/039786 (Innogenetics) discloses specific uses of polypeptides denominated as suppressive macrophage activation factors (SMAF's) wherein SMAF-1 is 100% identical to Cometin. Specifically, it is disclosed that SMAF-1 and/or SMAF-2 modulate the production of Th1, Th2 and/or Th3 cytokines and indicates how SMAF-1 molecules can be used to treat diseases mediated by type 1, type 2 and/or type 3 responses such as inflammation, infections, allergies, autoimmune diseases, transplant rejections, graft-versus-host disease, malignancies and diseases involving mucosal immunity.

WO 2010/009732 (NsGene) describes Cometin (under the name Meteorin-like or METRNL) as a neurotrophic growth factor with effects on neurite outgrowth in dorsal root ganglion explants, on neurblast migration in subventricular zone explants and with effects in an animal model of hearing loss.

SUMMARY OF INVENTION

The present invention provides methods for treatment of allodynia, hyperalgesia, spontaneous pain and phantom pain. The methods use Cometin protein, nucleotide sequences encoding Cometin, expression vectors comprising the nucleotide sequence encoding Cometin, cell lines transformed/transfected with the expression vector encoding Cometin, or biocompatible capsule delivering secreted Cometin.

Thus, in a first aspect the present invention relates to an isolated polypeptide for use in a method of treatment of allodynia, hyperalgesia, spontaneous pain and/or phantom pain, said polypeptide comprising an amino acid sequence selected from the group consisting of:
  i. The amino acid sequence of SEQ ID NO: 7;
  ii. A biologically active sequence variant of the amino acid sequence of SEQ ID NO:7, wherein the variant has at least 70% sequence identity to SEQ ID NO 7; and
  iii. A biologically active fragment of at least 50 contiguous amino acids of a) or b) wherein the fragment is at least 70% identical to SEQ ID NO: 7.

The inventors have found that Cometin is capable of alleviating hypersensitivity in an animal model of both thermal and mechanical allodynia. Importantly the animals did not experience any weight loss or signs of toxicity over the duration of the experiment and no painful side effects were observed.

In a further aspect the invention relates to an isolated nucleic acid molecule for use in a method of treatment of allodynia, hyperalgesia, spontaneous pain and/or phantom pain, said nucleic acid molecule comprising a nucleic acid sequence encoding a polypeptide, said polypeptide comprising an amino acid sequence selected from the group consisting of:
  i. The amino acid sequence of SEQ ID NO: 7;
  ii. A biologically active sequence variant of the amino acid sequence of SEQ ID NO:7, wherein the variant has at least 70% sequence identity to SEQ ID NO 7; and
  iii. A biologically active fragment of at least 50 contiguous amino acids of a) or b) wherein the fragment is at least 70% identical to SEQ ID NO: 7.

In a further aspect the invention relates to an expression vector comprising a nucleic acid molecule of the invention for use in a method of treatment of allodynia, hyperalgesia, spontaneous pain and/or phantom pain.

In a still further aspect the invention relates to an isolated host cell comprising an expression vector according to the invention for use in a method of treatment of allodynia, hyperalgesia, spontaneous pain and/or phantom pain. In particular the invention relates to host cells useful for cell based therapy; either naked cell based therapy or encapsulated cell therapy for use in a method of treatment of allodynia, hyperalgesia, spontaneous pain and/or phantom pain.

In a further aspect the invention relates to an implantable biocompatible capsule for use in a method of treatment of allodynia, hyperalgesia, spontaneous pain and/or phantom pain by delivery of secreted biologically active Cometin to a subject, said capsule comprising:
  i. A biocompatible outer membrane and an inner core,
  ii. Said inner core comprising cells according to the invention.

In a further aspect the invention relates to a composition comprising:
  i. The isolated polypeptide according to the invention; or
  ii. The isolated nucleic acid according to the invention; or
  iii. The expression vector according to the invention; or
  iv. The cell line according to the invention; or
  v. An implantable biocompatible capsule according to the invention;

for use in a method of treatment of allodynia, hyperalgesia, spontaneous pain and/or phantom pain.

In a further aspect the invention relates to a method of treatment of allodynia, hyperalgesia, spontaneous pain and/or phantom pain in a subject comprising administrating to said subject in need thereof a therapeutically effective amounts of a Cometin polypeptide according to the invention.

DESCRIPTION OF DRAWINGS

Figure Legends

FIG. 1: Alignment of human, mouse and rat Cometin protein (SEQ ID NO 2, 4, and 6). Predicted signal peptide in bold. Alignments were made using CLUSTAL W (1.7) (Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680.). BLOSUM 62 was used as scoring matrix.

| Sequence | Start | End | Match | NonMatch | % Match |
|---|---|---|---|---|---|
| hCometin | 1 | 311 | | | |
| mCometin | 1 | 311 | 241 | 70 | 77 |
| rCometin | 1 | 311 | 243 | 68 | 78 |

FIG. 2: Alignment of human, mouse, and rat Cometin (SEQ ID NO 2, 4, and 6) and human, mouse and rat Meteorin (SEQ ID NO 23, 24, and 25). Signal peptide in bold. Conserved Cys residues boxed. Clustal W (1.7) was used for alignment.

| Sequence | Start | End | Match | NonMatch | % Match |
|---|---|---|---|---|---|
| hCometin | 1 | 311 | | | |
| mCometin | 1 | 311 | 241 | 70 | 77 |
| rCometin | 1 | 311 | 243 | 68 | 78 |
| hMETRN | 1 | 293 | 138 | 185 | 42 |
| mMETRN | 1 | 291 | 139 | 187 | 43 |
| rMETRN | 1 | 291 | 140 | 186 | 43 |

FIG. 3: Alignment of human (NP_001004431.1; SEQ ID NO 2), mouse (NP_659046.1; SEQ ID NO 4), rat (NP_001014126; SEQ ID NO 6), cow (XP_614019.3; SEQ ID NO 19), chicken (CR352488; SEQ ID NO 20), xenopus tropicalis (BX757299.1; SEQ ID NO 21) and zebrafish (NP_998150.1; SEQ ID NO 22) Cometin protein sequences. Conserved residues identical to the human sequence are shaded, predicted signal peptides are in bold, ten conserved cysteine residues are boxed and the conserved N-terminal Glutamine (Q) of the mature protein sequence marked by an arrow.

Figure 4:
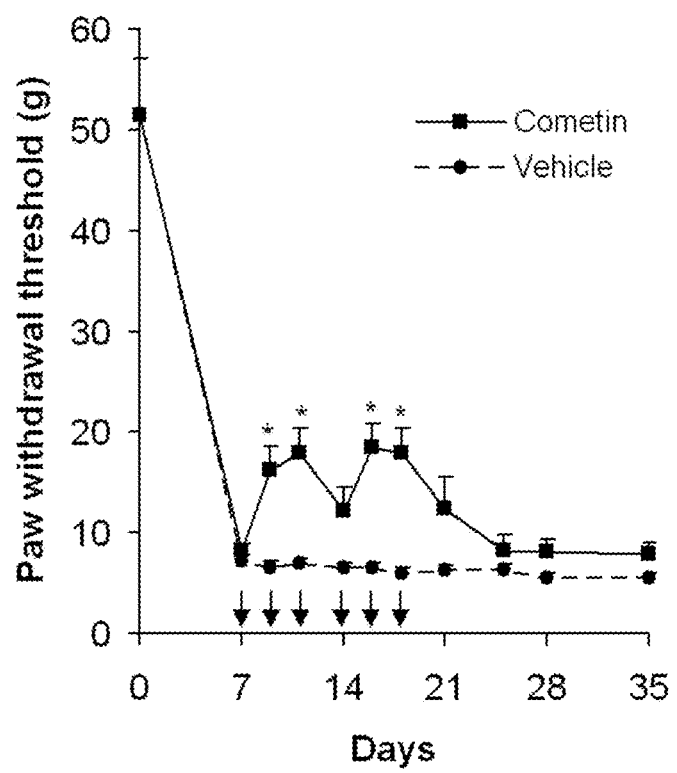

FIG. 4. Effect of Cometin on paw withdrawal threshold to mechanical stimulation following sciatic nerve injury. Arrows indicate time points for intrathecal injection. Data are shown as means±SEM.*p<0.05.

Figure 5:
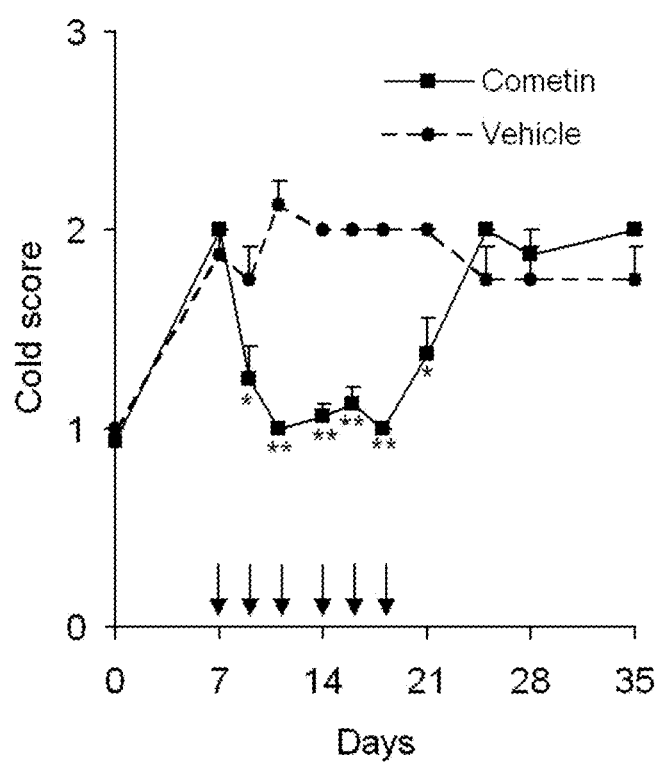

FIG. 5. Effect of Cometin on response to cold stimulation following sciatic nerve injury. Arrows indicate time points for intrathecal injection. Data are shown as means±SEM. *p<0.05 and **p<0.01.

Figure 6:
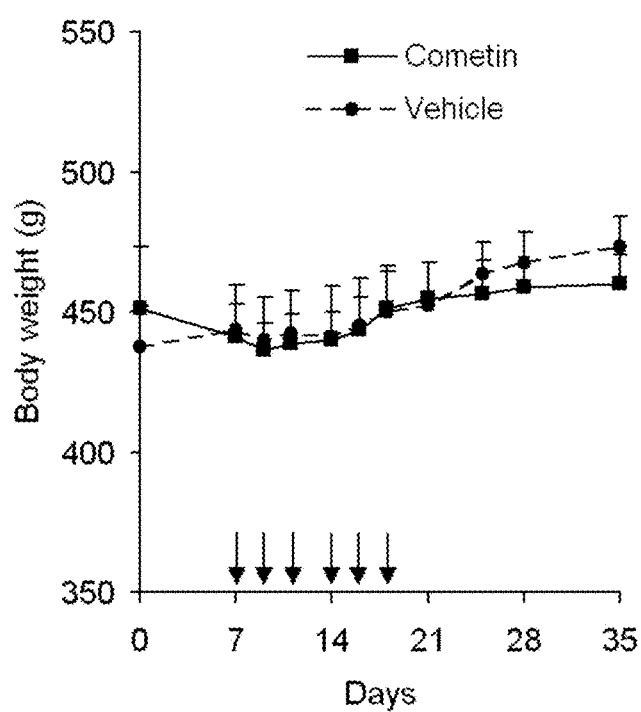

FIG. 6. Body weight in the experimental groups. Arrows indicate time points for intrathecal injection.

DETAILED DESCRIPTION OF THE INVENTION

Definitions

As used herein "a biocompatible capsule" means that the capsule, upon implantation in a host mammal, does not elicit a detrimental host response sufficient to result in the rejection of the capsule or to render it inoperable, for example through degradation.

As used herein, a "coding sequence" is a polynucleotide sequence which is transcribed and translated into a polypeptide.

A "deletion", as used herein, refers to a change in the amino acid or nucleotide sequence and results in the absence of one or more amino acid residues or nucleotides.

As used herein, the term "expression vectors" refers to vectors that are capable of directing the expression of genes to which they are operatively-linked. In general, expression vectors of utility in recombinant DNA techniques are often in the form of plasmids.

As used herein "an immunoisolatory capsule" means that the capsule upon implantation into a mammalian host minimizes the deleterious effects of the host's immune system on the cells within its core.

By a "mammalian promoter" is intended a promoter capable of functioning in a mammalian cell.

Cometin, as used herein, refers to polypeptides having the amino acid sequences of substantially purified Cometin obtained from any species, particularly mammalian, including chimpanzee, bovine, ovine, porcine, murine, equine, and preferably human, from any source whether natural, synthetic, semi-synthetic, or recombinant. The term also refers to biologically active fragments of Cometin obtained from any of these species, as well as to biologically active sequence variants of these and to proteins subject to post-translational modifications.

Biologically active fragments of Cometin may differ at one or more positions from the wildtype Cometin sequences, preferably at up to 20 of the positions, more preferably up to 10 positions, more preferably at up to 5 positions, such as at one, two, three or four positions.

Growth factor characteristics as used herein define sequence-related features similar to those of classical growth factors, which are secreted proteins acting on a target cell through a receptor to cause one or more of the following responses in the target cell: growth including proliferation, differentiation, survival, regeneration, migration, regain of function, improvement of function.

"Sequence identity": A high level of sequence identity indicates likelihood that the first sequence is derived from the second sequence. Amino acid sequence identity requires identical amino acid sequences between two aligned sequences. Thus, a candidate sequence sharing 70% amino acid identity with a reference sequence, requires that, following alignment, 70% of the amino acids in the candidate sequence are identical to the corresponding amino acids in the reference sequence. Identity may be determined by aid of computer analysis, such as, without limitations, the ClustalW computer alignment program (Higgins D., Thompson J., Gibson T., Thompson J. D., Higgins D. G., Gibson T. J., 1994. CLUSTAL W: improving the sensitivity of progressive multiple sequence alignment through sequence weighting, position-specific gap penalties and weight matrix choice. Nucleic Acids Res. 22:4673-4680), and the default parameters suggested therein. The ClustalW software is available as a ClustalW WWW Service at the European Bioinformatics Institute from http://www.ebi.ac.uk/clustalw.

Using this program with its default settings, the mature (bioactive) part of a query and a reference polypeptide are aligned. The number of fully conserved residues are counted and divided by the length of the reference polypeptide. In doing so, any tags or fusion protein sequences, which form part of the query sequence are disregarded in the alignment and subsequent determination of sequence identity.

The ClustalW algorithm may similarly be used to align nucleotide sequences. Sequence identities may be calculated in a similar way as indicated for amino acid sequences.

Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the FASTA sequence alignment software package (Pearson W R, Methods Mol Biol, 2000, 132:185-219). Align calculates sequence identities based on a global alignment. Align0 does not penalise to gaps in the end of the sequences. When utilizing the ALIGN og Align0 program for comparing amino acid sequences, a BLOSUM50 substitution matrix with gap opening/extension penalties of −12/−2 is preferably used.

The term "subject" used herein is taken to mean any mammal to which Cometin polypeptide or polynucleotide, therapeutic cells or biocompatible capsules may be administered. Subjects specifically intended for treatment with the method of the invention include humans, as well as nonhuman primates, sheep, horses, cattle, goats, pigs, dogs, cats, rabbits, guinea pigs, hamsters, gerbils, rats and mice, as well as the organs, tumors, and cells derived or originating from these hosts.

The term "substantially purified", as used herein, refers to nucleic or amino acid sequences that are removed from their natural environment, isolated or separated, and are at least 60% free, preferably 75% free, and most preferably 90% free from other components with which they are naturally associated.

An "insertion" or "addition", as used herein, refers to a change in an amino acid or nucleotide sequence resulting in the addition of one or more amino acid residues or nucleotides, respectively, as compared to the naturally occurring molecule.

A "substitution", as used herein, refers to the replacement of one or more amino acids or nucleotides by different amino acids or nucleotides, respectively.

"Treatment" can be performed in several different ways, including curative, ameliorating and as prophylaxis. Curative treatment generally aims at curing a clinical condition, such as a disease or an infection, which is already present in the treated individual. Ameliorating treatment generally means treating in order to improve, in an individual, an existing clinical condition. Prophylactic treatment generally aims at preventing a clinical condition or reducing the risk of contracting the condition or reducing the extent of the condition. The present invention relates to all these types of treatment.

As used herein, the term "vector" refers to a nucleic acid molecule capable of transporting another nucleic acid to which it has been linked. One type of vector is a "plasmid", which refers to a circular double stranded DNA loop into which additional DNA segments can be ligated. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

Allodynia

Allodynia, meaning "other power", is a pain due to a stimulus which does not normally provoke pain and can be either thermal or mechanical/tactile. It is pain from a stimulus that does not normally lead to the sensation of pain, and may occur after injury to a site. Allodynia is different from hyperalgesia and spontaneous pain, which is described in the section "hyperalgesia" and "spontaneous pain" respectively. Allodynia is a type of hypersensitivity.

There are different kinds or types of allodynia:
Mechanical allodynia (also known as tactile allodynia)
Static mechanical allodynia—pain in response to light touch/pressure
Dynamic mechanical allodynia—pain in response to brushing
Thermal (heat or cold) allodynia—pain from normally mild skin temperatures in the affected area Allodynia is a clinical feature of many painful conditions, such as neuropathies, complex regional pain syndrome, postherpetic neuralgia, fibromyalgia, and migraine. Allodynia may also be caused by some populations of stem cells used to treat nerve damage including spinal cord injury. In one embodiment of the present invention the allodynia to be treated is mechanical/tactile allodynia. In another embodiment of the present invention the allodynia to be treated is thermal allodynia. In a preferred embodiment of the present invention the allodynia to be treated is cold allodynia.

The cell types involved in nociception and mechanical sensation are the cells responsible for allodynia. In healthy individuals, nociceptors sense information about cell stress or damage and temperature at the skin and transmit it to the spinal cord. The cell bodies of these neurons lie in dorsal root ganglia, important structures located on both sides of the spinal cord. The axons then pass through the dorsal horn to make connections with secondary neurons. The secondary neurons cross over to the other (contralateral) side of the spinal cord and reach nuclei of the thalamus. From there, the information is carried through one or more neurons to the somatosensory cortex of the brain. Mechanoreceptors follow the same general pathway. However, they do not cross over at the level of the spinal cord, but at the lower medulla instead. In addition, they are grouped in tracts that are spatially distinct from the nociceptive tracts.

Despite this anatomical separation, mechanoreceptors can influence the output of nociceptors by making connections with the same interneurons, the activation of which can reduce or completely eliminate the sensation of pain. Another way to modulate the transmission of pain information is via descending fibers from the brain. These fibers act through different interneurons to block the transmission of information from the nociceptors to secondary neurons.

Both of these mechanisms for pain modulation have been implicated in the pathology of allodynia. Several studies suggest that injury to the spinal cord might lead to loss and re-organization of the nociceptors, mechanoreceptors and interneurons, leading to the transmission of pain information by mechanoreceptors. A different study reports the appearance of descending fibers at the injury site. All of these changes ultimately affect the circuitry inside the spinal cord, and the altered balance of signals probably leads to the intense sensation of pain associated with allodynia.

Different cell types have also been linked to allodynia. For example, there are reports that microglia in the thalamus might contribute to allodynia by changing the properties of the secondary nociceptors. The same effect is achieved in the spinal cord by the recruitment of immune system cells such as monocytes/macrophages and T lymphocytes.

As already mentioned, there are descending neurons that modulate the perception of pain. Many of these neurons originate in nuclei in the brainstem and pass through the periaqueductal gray (PAG) area of the midbrain.

The body possesses an additional mechanism to control pain: the release of endogenous opioids, especially at the level of the PAG. There are neurons that release enkephalins, endorphins, and dynorphins at the PAG, and in this way modulate its ability to modulate pain perception. Other neurons can release their endogenous opioids at the source of the pain, as well. If this occurs, the transmission of pain information from the nociceptors to the secondary neurons is blocked, and no pain is felt. Unfortunately, these endogenous mechanisms are often damaged and nonfunctional in people suffering from allodynia, so the application of pharmaceuticals is needed.

Numerous compounds alleviate the pain from allodynia. Some are specific for certain types of allodynia while others are general. They include non-steroidal anti-inflammatory drugs (NSAIDs), opioids, and compounds targeting different ion channels.

The present invention relates to the use of Cometin for treatment of allodynia. Preferably the allodynia to be treated is thermal allodynia, even more preferably the thermal allodynia to be treated is cold allodynia.

Hyperalgesia

Hyperalgesia is an extreme response to a stimulus which is normally perceived as painful. The stimulus can be mechanical/tactile or thermal.

Hyperalgesia is similar to other sorts of pain associated with nerve damage such as allodynia, and consequently may respond to standard treatment for this condition as described in the section "allodynia". Hyperalgesia may also be characterised as a type of hypersensitivity.

In one embodiment the present invention relates to the use of Cometin for treatment of hyperalgesia. In one embodiment the hyperalgesia to be treated is mechanical/tactile hyperalgesia. In another embodiment the hyperalgesia to be treated is thermal hyperalgesia, preferably cold hyperalgesia. Together, allodynia and hyperalgesia may be characterised as hypersensitivity.

Spontaneous Pain

Spontaneous pain is characterized by being pain occurring without any trigger. The clinical symptoms of spontaneous pain include sensations of pins and needles, shooting, burning, stabbing and paroxysmal (electric shock-like) pain sometimes associated with dysesthesia and/or paresthesia. Dysesthesia is defined as an unpleasant, abnormal sense of touch, and it may be considered as a kind of pain occurring spontaneously. Paresthesia is defined as a sensation of tingling, pricking or numbness of a subjects skin with no apparent long-term physical effect. Spontaneous pain seems likely to be caused by spontaneous activity of neurons in the afferent pathway.

In one embodiment the present invention relates to the use of Cometin for treatment of spontaneous pain.

Phantom Pain

Phantom pain sensations are described as perceptions that a subject experiences relating to a limb or an organ that is not physically part of the body. Phantom pain sensations are recorded most frequently following the amputation of an arm or a leg, but may also occur following the removal of a breast or an internal organ. The phantom pain sensation varies from individual to individual. Phantom pain can be experienced as sensations related to movement, touch, temperature, pressure and itchiness.

In one embodiment the present invention relates to the use of Cometin for treatment of phantom pain.

Causes of Allodynia, and Hyperalgesia

Allodynia, hyperalgesia and in general hypersensitivity can arise from a variety of disorders, some of which are listed below.

| Class | Sub-type of cause |
|---|---|
| Traumatic mechanical injury | Entrapment neuropathy |
| | Nerve transection |
| | Spinal cord injury |
| | Post-surgical pain |
| | Phantom limb pain |
| | Scar formation |
| | Sciatica |
| Metabolic or nutritional | Alcoholic neuropathy |
| | Pellagra |
| | Beriberi |
| | Burning foot syndrome |
| Viral | Post-herpetic neuralgia |
| | HIV/AIDS pain |
| Neurotoxicity | Vincristine |
| | Cisplatine |
| | Taxol |
| | Thallium |
| | Arsenic |
| | Radiation therapy |
| Disease (non-viral) | Diabetes |
| | Malignancies |
| | Multiple sclerosis |
| | Trigeminal neuralgia |
| | Guillain-Barre syndrome |
| | Fabry's disease |
| | Tangier disease |
| | Vasculitic/angiopathic |
| | Amyloid |
| | Idiopathic |
| Ischaemia | Sciatica |
| | Thalamic syndrome |
| | Post-stroke pain |
| Neurotransmitter function | Comples regional pain syndrome |

Thus in one embodiment the invention relates to treatment of allodynia, hyperalgesia, or hypersensitivity in a subject diagnosed with one of the disorders listed in the table above. Preferably, the invention relates to treatment of hypersensitivity in a subject diagnosed with painful diabetic neuropathy, post-herpetic neuralgia, and/or sciatica. More specifically, the invention relates to treatment of allodynia and hyperalgesia in a subject diagnosed with painful diabetic neuropathy, post-herpetic neuralgia, and/or sciatica. In a more preferred embodiment, the invention relates to treatment of allodynia in a subject diagnosed with painful diabetic neuropathy, post-herpetic neuralgia, and/or sciatica.

Method of Treatment

In one embodiment the present invention relates to the use of Cometin for the treatment of allodynia, hyperalgesia, spontaneous pain and/or phantom pain. In a more preferred embodiment the present invention relates to the use of Cometin for the treatment of allodynia, hyperalgesia and/or spontaneous pain. In an even one embodiment the present invention relates to the use of Cometin for treatment of hyperalgesia and/or allodynia.

In a preferred embodiment the present invention relates to the use of Cometin for treatment of allodynia. In a more preferred embodiment the present invention relates to the use of Cometin for treatment of mechanical allodynia. In another preferred embodiment the present invention relates to the use of Cometin for treatment of thermal allodynia. In an even more preferred embodiment of the present invention the thermal allodynia is cold allodynia.

In another preferred embodiment, the present invention relates to the use of Cometin for the treatment of spontaneous pain.

In another preferred embodiment the present invention relates to the use of Cometin for the treatment of hyperalgesia. In a more preferred embodiment the present invention relates to the use of Cometin for the treatment of mechanical hyperalgesia. In another preferred embodiment, the present invention relates to the use of Cometin for the treatment of thermal hyperalgesia. In an even more preferred embodiment of the present invention the hyperalgesia is cold hyperalgesia.

Thus, in general Cometin may be used to treat hypersensitivity.

Polypeptide Administration and Formulations

Cometin polypeptides may be administered in any manner, which is medically acceptable. This may include injections, by parenteral routes such as intravenous, intravascular, intraarterial, subcutaneous, intramuscular, intratumor, intraperitoneal, intraventricular, intraepidural, intrathecal, intracerebroventricular, intercerebral, or others as well as nasal, or topical. Slow release administration is also specifically included in the invention, by such means as depot injections or erodible implants.

Administration of Cometin according to this invention may be achieved using any suitable delivery means, including:

injection, either subcutaneously, intravenously, intra-arterially, intramuscularly, intrathecally or to other suitable site;
continuous infusion (intrethecal catheter);
microencapsulation, or slow release polymer implants;
encapsulated cells and unencapsulated cell grafts (e.g. ex vivo gene therapy); and
inhalation.

Administration may be by periodic injections of a bolus of the preparation, or may be made more continuous by intravenous or intraperitoneal administration from a reservoir which is external (e.g., an IV bag) or internal (e.g., a bioerodable implant, a bioartificial organ, a biocompatible capsule of Cometin production cells, or a colony of implanted Cometin production cells). See, e.g., U.S. Pat. Nos. 4,407,957, 5,798,113, and 5,800,828, each incorporated herein by reference.

Localised delivery may be by such means as delivery via a catheter to one or more arteries or intrathecally. In one embodiment of the present invention localised delivery comprises delivery using encapsulated cells. A further type of localised delivery comprises local delivery of gene therapy vectors, which are normally injected.

In a preferred embodiment of the present invention the administration is parenteral injection, preferably subcutaneous injection or intrathecal injection.

Whilst it is possible for the compounds of the present invention to be administered as the raw chemical, it is preferred to present them in the form of a pharmaceutical formulation. The pharmaceutical formulations may be prepared by conventional techniques, e.g. as described in Remington: The Science and Practice of Pharmacy 2005, Lippincott, Williams & Wilkins.

The term "pharmaceutically acceptable carrier" means one or more organic or inorganic ingredients, natural or synthetic, with which Cometin polypeptide is combined to facilitate its application. A suitable carrier includes sterile saline although other aqueous and non-aqueous isotonic sterile solutions and sterile suspensions known to be pharmaceutically acceptable are known to those of ordinary skill in the art.

The compounds of the present invention may be formulated for parenteral administration and may be presented in unit dose form in ampoules, pre-filled syringes, small volume infusion or in multi-dose containers, optionally with an added preservative. The compositions may take such forms as suspensions, solutions, or emulsions in oily or aqueous vehicles, for example solutions in aqueous polyethylene glycol. Examples of oily or non-aqueous carriers, diluents, solvents or vehicles include propylene glycol, polyethylene glycol, vegetable oils (e.g., olive oil), and injectable organic esters (e.g., ethyl oleate), and may contain agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

Liposomes may be used for targeted delivery of a cometin polypeptide. A liposome system may be any variety of unilamellar vesicles, multilamellar vesicles, or stable plurilamellar vesicles, and may be prepared and administered according to methods well known to those of skill in the art. The liposome-encapsulated protein may be tested in vitro for any effect on target cells, e.g. DRGs.

Where slow-release administration of a Cometin polypeptide is desired in a formulation with release characteristics suitable for the treatment of any disease or disorder requiring administration of a Cometin polypeptide, microencapsulation of a Cometin polypeptide is contemplated.

In one embodiment of the present invention a composition comprising Cometin is contemplated. The composition may comprise an isolated polypeptide as described herein, an isolated nucleic acid as described herein, a Cometin encoding expression vector as described herein, a cell line expressing Cometin as described herein or a biocompatible capsule secreting Cometin as described herein.

Dosages

Various dosing regimes for systemic administration are contemplated. In one embodiment, methods of administering to a subject a formulation comprising a Cometin polypeptide include administering Cometin at a dosage of between 1 µg/kg to 10,000 µg/kg body weight of the subject, per dose. In another embodiment, the dosage is between 1 µg/kg to 7,500 µg/kg body weight of the subject, per dose. In a further embodiment, the dosage is between 1 µg/kg to 5,000 µg/kg body weight of the subject, per dose. In a different embodiment, the dosage is between 1 µg/kg to 2,000 µg/kg body weight of the subject, per dose. In yet another embodiment, the dosage is between 1 µg/kg to 1,000 µg/kg body weight of the subject, per dose. In yet another embodiment, the dosage is between 1 µg/kg to 700 µg/kg body weight of the subject, per dose. In a more preferable embodiment, the dosage is between 5 µg/kg to 500 µg/kg body weight of the subject, per dose. In a most preferable embodiment, the dosage is between 10 µg/kg to 100 µg/kg body weight of the subject, per dose. In a preferred embodiment the subject to be treated is human.

Guidance as to particular dosages and methods of delivery is provided in the literature; see, for example, WO 02/78730 and WO 07/100898. Guidance to the calculation of the human equivalent dosages based on dosages used in animal experiments is provided in Reagan-Shaw et al., FASEB J, 22, 659-661 (2007).

The dose administered must be carefully adjusted to the age, weight and condition of the individual being treated, as well as the route of administration, dosage form and regimen, and the result desired, and the exact dosage should be determined by the practitioner.

In one embodiment of the present invention the administration is repeated daily. In another embodiment the administration is repeated at least 1-3 times weekly, such as 2-5 times weekly, such as 3-6 times weekly.

Cometin

The present invention relates to the medical use of polypeptides and polynucleotides being identified as Cometin protein and polynucleotides encoding said protein, in the treatment of allodynia, hyperalgesia, spontaneous pain and/or phantom pain. The delivery is in one embodiment contemplated to be by use of a capsule for delivery of a secreted biologically active Cometin and/or a homologue thereof to a subject. The Cometin protein has been identified in human beings (SEQ ID No. 2), mouse (SEQ ID No. 4), and rat (SEQ ID No. 6) and a variety of other species. The Cometin protein has been identified in human beings (SEQ ID No. 2), mouse (SEQ ID No. 4), and rat (SEQ ID No. 6), as well as cow (SEQ ID NO 19), chicken (SEQ ID NO 20), *Xenopus tropicalis* (SEQ ID NO 21), and Zebrafish (SEQ ID NO 22) (FIG. 3).

Human Cometin exists as a 311 amino acid precursor, which can be processed to give rise to at least one biologically active peptide. Cometin appears not to be expressed at high levels in any adult tissues but is expressed in certain tissues at high levels during foetal development (Jorgensen et al, 2012, Exp Neurol 233:172-81). The mouse (SEQ ID No 4) and rat (SEQ ID No 6) Cometin polypeptides likewise consist of 311 amino acids, respectively and the % identities with the human protein are 77 and 78, respectively—calculated for the full length sequences.

Mouse Cometin contains an N-terminal signal peptide sequence of 45 amino acids, which is cleaved at the sequence motif ASA-QY. This signal peptide cleavage site is predicted by the SignalP method and has been verified experimentally by Mass Spectometry. An identical cleavage site is predicted in the human and rat proteins. Cleavage of the signal peptide results in polypeptides having SEQ ID No. 7, 8, and 9 for human, mouse, and rat respectively. As it is known in the art, signal peptide processing is not always exactly as predicted and actual cleavage may vary from case to case. Thus, it is expected that the N-terminal of mature Cometin may vary by one to two or three amino acids from the predicted cleavage site.

As it is known in the art, an N-terminal glutamine may be cyclized to pyroglutamic acid. Thus, in one embodiment Cometin contains a cyclized N-terminal glutamine.

Cometin is structurally related to METRN (NsG33, Meteorin) protein described in WO 2005/095450 (NsGene). The full length human, mouse and rat proteins are shown in FIG. 2. METRN shares 42/43% identity (Clustal W (1.7) with standard settings) to the human Cometin protein.

A full length alignment of human Cometin to METRN protein is shown in FIG. 2. Ten conserved cysteines are boxed. The two proteins together form a protein family based on the conserved cysteine residues and the stretches of high conservation which are evident from FIG. 2. None of the two proteins show any significant sequence homology to any other known human proteins. Although the two proteins are members of the same small protein family, the two proteins are structurally distinct.

Due to the high conservation of the cysteines, it is expected that these residues play an important role in the secondary and tertiary structure of the bioactive protein. One or more of the cysteines may participate in the formation of intra- and/or intermolecular cystine-bridges.

Cometin belongs to the category of proteins acting as growth factors. This notion is supported by the fact that the protein is secreted, by its structural features (relatively small protein with a conserved cysteine pattern), and by the fact that it exerts growth factor effects on target cells. Furthermore Cometin is structurally related to the growth factor METRN.

The therapeutic effect of Cometin may be mediated through an effect on growth including proliferation, regeneration, regain of function, improvement of function, survival, migration, and/or differentiation of targeted cells.

It has been demonstrated that Cometin administered by repeated intrathecal injections significantly reduced mechanical and cold hypersensitivity in rats after sciatic nerve injury (see Example 2). Cometin also has a stimulating effect on neurite outgrowth in dorsal root ganglion cells and stimulated migration in subventricular zone explants (see WO 2010/009732).

Cometin Polypeptides

In addition to full-length Cometin, substantially full-length Cometin, and to truncated Cometin, the present invention provides for biologically active fragments and sequence variants of these polypeptides. A Cometin polypeptide, a sequence variant, or fragment is biologically active if it exhibits a biological activity of naturally occurring Cometin. Biologically active fragments of Cometin may differ at one or more positions from the wildtype Cometin sequences at up to 20 of the positions, more preferably up to 10 positions, more preferably at up to 5 positions, such as at one, two, three or four positions. It is to be understood that the invention relates to substantially purified Cometin as herein defined.

One biological activity is the ability to compete with naturally occurring Cometin in a receptor-binding assay.

Another biological activity is the ability to bind to an antibody, which is directed at an epitope, which is present on naturally occurring Cometin.

Biologically active variants may also be defined with reference to one or more of the biological assays described in the examples.

A preferred biological activity is the ability to elicit substantially the same response as in the DRG assay described in the Example 2 and FIG. 6 of WO 2010/009732. In this assay, cultures of dissociated rat P5 DRGs are exposed to murine Cometin protein (SEQ ID NO 8 of WO 2010/009732) with a C-terminal his-tag (SEQ ID NO 26 of WO 2010/009732). By substantially the same response in the DRG assay is intended that the neurite length per cell is at least 10% of the number obtained for C-terminally his-tagged mouse Cometin in Example 2 of WO 2010/009732, more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%.

The results in FIG. 6 of WO 2010/009732 may also be calculated as the percentage or number of neurite bearing cells. In that case, substantially the same response in the DRG assay is intended that the number of neurite bearing cells is at least 10% of the number obtained in Example 2 of WO 2010/009732, more preferably at least 20%, more preferably at least 30%, more preferably at least 40%, more preferably at least 50%, more preferably at least 60%, more preferably at least 70%, more preferably at least 75%, more preferably at least 80%, more preferably at least 85%, more preferably at least 90%. The biological activity of a fragment or variant of Cometin may also be higher than that of the naturally occurring Cometin.

Specific preferred truncated forms of Cometin in one aspect, are selected from the group consisting of:
i) A polypeptide having an amino acid sequence as set forth in SEQ ID No 10, and polypeptides having from one to five extra amino acids;
ii) A polypeptide having an amino acid sequence as set forth in SEQ ID No 11, and polypeptides having from one to five extra amino acids;
iii) A polypeptide having an amino acid sequence as set forth in SEQ ID No 12, and polypeptides having from one to five extra amino acids; and
iv) variants of said polypeptides, wherein any amino acid specified in the chosen sequence is changed to a different amino acid, provided that no more than 20 of the amino acid residues in the sequence are so changed.

These truncated forms of Cometin comprise a core sequence from the first to the last conserved cysteine. In a preferred embodiment, less than 15 amino acids have been changed, more preferably less than 10 amino acids, more preferably less than 5 amino acids, such as 1 or 2 amino acids, more preferably no amino acids have been changed.

Variants can differ from naturally occurring Cometin in amino acid sequence or in ways that do not involve sequence, or in both ways. Variants in amino acid sequence ("sequence variants") are produced when one or more amino acids in naturally occurring Cometin is substituted with a different natural amino acid, an amino acid derivative or non-native amino acid. Particularly preferred variants include naturally occurring Cometin, or biologically active fragments of naturally occurring Cometin, whose sequences differ from the wild type sequence by one or more conservative and/or semi-conservative amino acid substitutions, which typically have minimal influence on the secondary and tertiary structure and hydrophobic nature of the protein or peptide. Variants may also have sequences, which differ by one or more non-conservative amino acid substitutions, deletions or insertions, which do not abolish the Cometin biological activity. The Clustal W alignment in FIG. 1 and/or FIG. 2 can be used to predict which amino acid residues can be substituted without substantially affecting the biological activity of the protein.

Substitutions within the following groups (Clustal W, 'strong' conservation group) are to be regarded as conservative substitutions within the meaning of the present invention
-STA, NEQK, NHQK, NDEQ, QHRK, MILV, MILF, HY, FYW.

Substitutions within the following groups (Clustal W, 'weak' conservation group) are to be regarded as semi-conservative substitutions within the meaning of the present invention
-CSA, ATV, SAG, STNK, STPA, SGND, SNDEQK, NDEQHK, NEQHRK, VLIM, HFY.

Other variants within the invention are those with modifications which increase peptide stability. Such variants may contain, for example, one or more nonpeptide bonds (which replace the peptide bonds) in the peptide sequence. Also included are: variants that include residues other than naturally occurring L-amino acids, such as D-amino acids or non-naturally occurring or synthetic amino acids such as beta or gamma amino acids and cyclic variants. Incorporation of D-instead of L-amino acids into the polypeptide may increase its resistance to proteases. See, e. g., U.S. Pat. No. 5,219,990. Splice variants are specifically included in the invention.

One particularly preferred mutation is the substitution of the N-terminal Gln residue found in all mature Cometin sequences (see e.g. FIG. 3) for another amino acid selected from the group consisting of naturally occurring amino acids except Gln and Cys. Preferably the residue is mutated into a non-hydrophobic residue. More preferably the residue is mutated into Asn, or Ala. These N-terminally mutated Cometin polypeptide avoid cyclisation of the N-terminal Gln residue into pyroglutamic acid. This cyclisation has the result that the polypeptide cannot be subjected to routine N-terminal sequencing.

When the result of a given substitution cannot be predicted with certainty, the derivatives may be readily assayed according to the methods disclosed herein to determine the presence or absence of biological activity. Preferably in the DRG assay described in WO 2010/009732.

In one embodiment, the polypeptide is a naturally occurring allelic variant of the sequence selected from the group consisting of SEQ ID No. 2, 4, and 6. This polypeptide may comprise an amino acid sequence that is the translation of a nucleic acid sequence differing by a single nucleotide from a nucleic acid sequence selected from the group consisting of SEQ ID No. 1, 3, and 5.

A variant polypeptide as described herein, in one embodiment comprises a polypeptide wherein any amino acid specified in the chosen sequence is changed to provide a conservative substitution.

The signal peptide may be replaced by a heterologous signal peptide for expression.

Variants within the scope of the invention in one embodiment include proteins and peptides with amino acid sequences having at least 60 percent identity with human, murine or rat Cometin (SEQ ID NO: 2, 4, and 6). More preferably the sequence identity is at least 65%, more preferably at least 70%, more preferably at least 75%, more preferably at least 80%, more preferably at least 85%, more preferably at least 90%, more preferably at least 95%, more preferably at least 98%.

Preferred variants within the scope of the invention in one embodiment include proteins and peptides with amino acid sequences having at least 60 percent identity with a polypeptide having the sequence of SEQ ID NO: 7, 8, and 9. More preferably the sequence identity is at least 65%, more preferably at least 70%, more preferably at least 75%, more preferably at least 80%, more preferably at least 85%, more preferably at least 90%, more preferably at least 95%, more preferably at least 98%. SEQ ID No 7, 8, and 9 correspond to the mature proteins after cleavage of the signal peptide. Preferably the N-terminal glutamine residue has been converted into a pyrrolidone carboxylic acid.

Variants within the scope of the invention in one embodiment include proteins and peptides with amino acid sequences having at least 60 percent identity with a polypeptide having the sequence of SEQ ID NO: 10, 11, and 12. More preferably the sequence identity is at least 65%, more preferably at least 70%, more preferably at least 75%, more preferably at least 80%, more preferably at least 85%, more preferably at least 90%, more preferably at least 95%, more preferably at least 98%.

In a preferred embodiment the sequence identity of the variant Cometin is determined with reference to a human Cometin polypeptide (SEQ ID No 2, 7, or 10).

In one embodiment the percent sequence identity is calculated using global alignment (Align), so that the variant and SEQ ID sequences are aligned, the total number of identical amino acid residues calculated and divided by the length of the SEQ ID NO under default settings of the used program.

In one embodiment, a variant Cometin comprises a naturally occurring allelic variant of the sequence selected from the group consisting of SEQ ID No 2, 4, and 6. Said allelic variant sequence may be an amino acid sequence that is the translation of a nucleic acid sequence differing by a single nucleotide from a nucleic acid sequence selected from the group consisting of SEQ ID No 1, 3, and 5.

In one embodiment, the variants include proteins comprising an amino acid sequence having at least 60% sequence identity to SEQ ID NO 7, more preferably at least 65%, more preferably at least 70%, more preferably at least 75%, more preferably at least 80%, more preferably at least 85%, more preferably at least 90%, more preferably at least 95%, more preferably at least 98%.

In one embodiment, a variant Cometin at corresponding positions comprises the residues marked in FIG. 1 or 2 as fully conserved (*), more preferably a variant Cometin also comprises at corresponding positions the residues that are strongly conserved (: strongly conserved groups include: STA, NEQK, NHQK, NEDQ, QHRK, MILV, MILF, HY FYW), more preferably a variant Cometin also comprises at corresponding positions the residues being less conserved (. less conserved groups include: CSA, ATV, SAG, STNK, STPA, SGND, SNDEQK, NDEQHK, NEQHK, NEQHRK, VLIM, HFY). In particular, it is contemplated that the conserved cysteines (FIG. 2) must be located at corresponding positions maintaining the spacing found in wildtype Cometin in a variant Cometin.

The fully conserved residues marked in FIG. 1 together constitute a consensus sequence. The consensus sequence may be regarded as a domain of Cometin which is important for bioactivity. As the signal peptide is cleaved from the polypeptide before it is used, amino acids of the signal peptide do not form part of the consensus sequence. Amino acids of the consensus sequence are less likely to tolerate substitutions and/or deletions than the remaining amino acids. In a preferred embodiment, only conservative substitutions are made to amino acids of the consensus sequence. In a more preferred embodiment, a variant neurotrophic Cometin polypeptide comprises the amino acids of the consensus sequence identified in FIG. 1.

Non-sequence modifications may include, for example, in vivo or in vitro chemical derivatisation of portions of naturally occurring Cometin, as well as acetylation, methylation, phosphorylation, carboxylation, sulfation, amino acid conjugation, GSH conjugation, oxidation, reduction, hydrolysis, PEG-ylation, or glycosylation. Just as it is possible to replace substituents of the protein, it is also possible to substitute functional groups, which are bound to the protein with groups characterized by similar features. Such modifications do not alter primary sequence. These will initially be conservative, i.e., the replacement group will have approximately the same size, shape, hydrophobicity and charge as the original group.

Many amino acids, including the terminal amino acids, may be modified in a given polypeptide, either by natural processes such as glycosylation and other post-translational modifications, or by chemical modification techniques which are well known in the art. Among the known modifications which may be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, I. E. Creighton, Proteins-Structure and Molecular Properties, 2nd Ed., W. H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Seifter et al., Meth. Enzymol. 182: 626-646, 1990 and Rattan et al., Protein Synthesis: Posttranslational Modifications and Aging, Ann. N.Y. Acad. Sci. 663: 48-62, 1992.

In addition, the protein may comprise a protein tag to allow subsequent purification and optionally removal of the tag using an endopeptidase. The tag may also comprise a protease cleavage site to facilitate subsequent removal of the tag. Non-limiting examples of affinity tags include a polyhis tag, a GST tag, a HA tag, a Flag tag, a C-myc tag, a HSV tag, a V5 tag, a maltose binding protein tag, a cellulose binding domain tag. Preferably for production and purification, the tag is a polyhistag. Preferably, the tag is in the C-terminal portion of the protein, such as at the very C-terminal.

The native signal sequence of Cometin may also be replaced in order to increase secretion of the protein in recombinant production in other mammalian cell types.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli*, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, glycosylation often does not occur in bacterial hosts such as *E. coli*.

Accordingly, when glycosylation is desired, a polypeptide should be expressed in a glycosylating host, generally a eukaryotic cell. Insect cells often carry out the same post-translational glycosylations as mammalian cells and, for this reason, insect cell expression systems have been developed to efficiently express mammalian proteins having native patterns of glycosylation, inter alia. Similar considerations apply to other modifications.

It will be appreciated that the same type of modification may be present to the same or varying degree at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

Cometin Nucleotide Sequences

The invention provides medical use of cDNA coding for Cometin, including for example the nucleotide sequence of human, mouse and rat Cometin cDNA (SEQ ID NO 1, 3, and 5,), the sequences coding for Cometin (SEQ ID NO 13, 14, and 15), and the sequences coding for Cometin without signal peptide (SEQ ID NO 16 or nucleotides 136-936 of SEQ ID No 1, SEQ ID NO 17 or nucleotides 136-936 of SEQ ID No. 3, and SEQ ID NO 18 or nucleotides 136-936 of SEQ ID No. 5).

Variants of these sequences are also included within the scope of the present invention.

The invention relates to an isolated nucleic acid molecule for medical use comprising a nucleic acid sequence encoding a polypeptide or its complementary sequence, said polypeptide comprising an amino acid sequence selected from the group consisting of:
 a) the amino acid sequence selected of SEQ ID No. 7;
 b) a sequence variant of the amino acid sequence of SEQ ID No. 7 wherein the variant has at least 70% sequence identity to SEQ ID No 7; and
 c) a biologically active fragment of at least 50 contiguous amino acids of any of a) through b), wherein the fragment has at least 70% sequence identity to SEQ ID No 7.

The nucleic acid molecule may comprise the nucleotide sequence of a naturally occurring allelic nucleic acid variant.

The nucleic acid molecule of the invention may encode a variant polypeptide, wherein the variant polypeptide has the polypeptide sequence of a naturally occurring polypeptide variant.

In one embodiment the nucleic acid molecule differs by a single nucleotide from a nucleic acid sequence selected from the group consisting of SEQ ID No. 1, 3, 5, 13, 14, 15, 16, 17, and 18.

Preferably the encoded polypeptide has at least 60% sequence identity to a sequence selected from the group consisting of SEQ ID No. 2, 7, and 10 preferably at least 65% sequence identity, more preferably at least 70% sequence identity, more preferably, 75% sequence identity, more preferably at least 80% sequence identity, more preferably at least 85% sequence identity, more preferably at least 90% sequence identity, more preferably at least 95% sequence identity, more preferably at least 98% sequence identify, more preferably wherein the polypeptide has a sequence selected from the group consisting of said SEQ ID No.s. Said sequences constitute human Cometin.

In a preferred embodiment the encoded polypeptide has at least 70% sequence identity to SEQ ID No. 7, more preferably at least 75%, more preferably at least 80%, more preferably at least 95%, more preferably at least 98%, more preferably wherein said polypeptide has the sequence of SEQ ID No. 7.

In one aspect the nucleic acid molecule comprises a nucleotide sequence selected from the group consisting of
 a) the nucleotide sequence selected from the group consisting of SEQ ID No. 1, 13, and 16;
 b) a nucleotide sequence having at least 70% sequence identity to a nucleotide sequence selected from the group consisting of SEQ ID No. 1, 13, and 16;
 c) a nucleic acid sequence of at least 150 contiguous nucleotides of a sequence selected from the group consisting of SEQ ID No. 1, 13, and 16.

SEQ ID No 7, 8 and 9 represent the sequences of mature Cometin polypeptides from human, mouse and rat. For recombinant expression in a eukaryotic expression system, these are preferably ligated to appropriate signal sequence coding sequences to ensure that the Cometin polypeptide is secreted from the cells. The same applies for recombinant expression of polypeptides defined by SEQ ID NO 10, 11, and 12.

In one preferred embodiment, the isolated polynucleotide of the invention has at least 50%, preferably at least 60%, more preferably at least 70%, more preferably at least 75%, more preferably at least 80%, preferably at least 85%, more preferred at least 90%, more preferred at least 95%, more preferred at least 98% sequence identity to a polynucleotide sequence presented as SEQ ID NO: 16.

A preferred group of isolated polynucleotides include SEQ ID No 1, 13, and 16, which are human Cometin polynucleotides. Another preferred group of isolated polynucleotides include SEQ ID No. 1, 3, and 5, which represent the cDNA sequences.

In addition, the nucleotide sequences of the invention include sequences, which are derivatives of these sequences. The invention also includes vectors, liposomes and other carrier vehicles, which encompass one of these sequences or a derivative of one of these sequences. The invention also includes proteins transcribed and translated from Cometin cDNA, preferably human Cometin cDNA, including but not limited to human Cometin and fragments and variants.

In another embodiment, the invention relates to an RNA counterpart of the DNA nucleic acid of Cometin. In particular, it relates to RNA counterparts of SEQ ID NO: 1, SEQ ID NO: 3, SEQ ID NO: 5, SEQ ID NO: 13, SEQ ID No. 14, SEQ ID No. 15, SEQ ID No 16, SEQ ID No 17, or SEQ ID No 18. Similarly the use of LNA or PNA counterparts of said SEQ ID No is contemplated.

Codon optimised nucleic acid molecules for enhanced expression in selected host cells, including but not limited to E. coli, yeast species, Chinese Hamster, Baby Hamster, insect, and fungus are also contemplated.

Variant nucleic acids can be made by state of the art mutagenesis methods. Methods for shuffling coding sequences from human with those of mouse, rat or chimpanzee are also contemplated. Specifically a shuffled variant may be between SEQ ID No 1 on one hand and 3 and/or 5 on the other hand. Also included are shuffled variants between SEQ ID No 3 and 5.

Pharmaceutical Preparations for Gene Therapy

To form a Cometin composition for gene therapy use in the invention, Cometin encoding expression viral vectors may be placed into a pharmaceutically acceptable suspension, solution or emulsion. Suitable mediums include saline and liposomal preparations.

More specifically, pharmaceutically acceptable carriers may include sterile aqueous of non-aqueous solutions, suspensions, and emulsions. Examples of nonaqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils.

Intravenous vehicles include fluid and nutrient replenishers, electrolyte replenishers (such as those based on Ringer's dextrose), and the like.

Viral Vectors

Ex vivo gene therapy approaches involve modification of isolated cells (including but not limited to stem cells, neural and glial precursor cells, and foetal stem cells), which are then infused, grafted or otherwise transplanted into the patient. See, e.g., U.S. Pat. Nos. 4,868,116, 5,399,346 and 5,460,959. In vivo gene therapy seeks to directly target host patient tissue.

Viruses useful as gene transfer vectors include papovavirus, adenovirus, vaccinia virus, adeno-associated virus, herpesvirus, and retroviruses. Suitable retroviruses include the group consisting of HIV, SIV, FIV, EIAV, MoMLV. A further group of suitable retroviruses includes the group consisting of HIV, SIV, FIV, EAIV, CIV. Another group of preferred virus vectors includes the group consisting of alphavirus, adenovirus, adeno associated virus, baculovirus, HSV, coronavirus, Bovine papilloma virus, Mo-MLV, preferably adeno associated virus.

Preferred viruses for treatment of disorders of the nervous system are lentiviruses and adeno-associated viruses. Both types of viruses can integrate into the genome without cell divisions, and both types have been tested in pre-clinical animal studies for indications of the nervous system, in particular the central nervous system.

Methods for preparation of AAV are described in the art, e.g. U.S. Pat. Nos. 5,677,158. 6,309,634 and 6,683,058 describe examples of delivery of AAV to the central nervous system.

Biocompatible Capsules

Encapsulated cell therapy is based on the concept of isolating cells from the recipient host's immune system by surrounding the cells with a semipermeable biocompatible material before implantation within the host. The invention includes use of a device in which cells capable of expressing and secreting Cometin are encapsulated in an immunoisolatory capsule as described in WO 2010/009732. An "immunoisolatory capsule" means that the capsule, upon implantation into a recipient host, minimizes the deleterious effects of the host's immune system on the cells in the core of the device. Cells are immunoisolated from the host by enclosing them within implantable polymeric capsules formed by a microporous membrane. This approach prevents the cell-to cell contact between host and implanted tissues, eliminating antigen recognition through direct presentation. The membranes used can also be tailored to control the diffusion of molecules, such as antibody and complement, based on their molecular weight. Useful biocompatible polymer capsules usually contain a core that contains cells, either suspended in a liquid medium or immobilized within an immobilizing matrix, and a surrounding or peripheral region of permselective matrix or membrane ("jacket") that does not contain isolated cells, that is biocompatible, and that is sufficient to protect cells in the core from detrimental immunological attack. Encapsulation hinders elements of the immune system from entering the capsule, thereby protecting the encapsulated cells from immune destruction. The semipermeable nature of the capsule membrane also permits the biologically active molecule of interest to easily diffuse from the capsule into the surrounding host tissue.

Preferably the capsule of this invention will be similar to those described in WO 92/19195 or WO 95/05452; or U.S. Pat. Nos. 5,639,275; 5,653,975; 4,892,538; 5,156,844; 5,283,187; or 5,550,050. Such capsules allow for the passage of metabolites, nutrients and therapeutic substances while minimizing the detrimental effects of the host immune system. Components of the biocompatible material may include a surrounding semipermeable membrane and the internal cell-supporting scaffolding. Preferably, the genetically altered cells are seeded onto the scaffolding, which is encapsulated by the permselective membrane.

The encapsulated cell devices are implanted according to known techniques. Many implantation sites are contemplated for the devices and methods of this invention. These implantation sites include, but are not limited to, the central nervous system, including the brain, spinal cord (see, U.S. Pat. Nos. 5,106,627, 5,156,844, and 5,554,148, incorporated by reference), and the aqueous and vitreous humors of the eye (see, WO 97/34586, incorporated by reference).

Recombinant Production and Purification of Cometin Polypeptides of the Invention The Cometin polypeptides of the invention may be produced using state of the art prokaryotic or eukaryotic expression systems. A eukaryotic expression system is described in Example 2 resulting in a substantially purified Cometin polypeptide.

Further exemplary methods are described in WO 93/22437 (Innogenetics), which is hereby incorporated by reference. The protocols described in WO 93/22437 describe purification of a protein having a predicted molecular weight of 29 kDa. In the case of expression of Cometin fragments, which may be considerably shorter, the protocols should be modified to take the difference in molecular weight into consideration.

Other state of the art protein purification protocols may also be used to provide enough pure protein to perform the in vitro and in vivo assays described in the examples.

EXAMPLES

Example 1

Example 1, Cometin Sequences

Sequence Listing Numbers.
SEQ ID NO 1: Human Cometin cDNA
SEQ ID NO 2: Human Cometin protein (incl. signal peptide)
SEQ ID NO 3: Mouse Cometin cDNA
SEQ ID NO 4: Mouse Cometin protein (incl. signal peptide)
SEQ ID NO 5: Rat Cometin cDNA
SEQ ID NO 6: Rat Cometin protein (incl. signal peptide)
SEQ ID NO 7: Human mature Cometin protein
SEQ ID NO 8: Mouse mature Cometin protein
SEQ ID NO 9: Rat mature Cometin protein
SEQ ID NO 10: Human Cometin core fragment
SEQ ID NO 11: Mouse Cometin core fragment
SEQ ID NO 12: Rat Cometin core fragment
SEQ ID NO 13: hCometin open reading frame
SEQ ID NO 14: mCometin open reading frame
SEQ ID NO 15: rCometin open reading frame
SEQ ID NO 16: Human CDS mature Cometin
SEQ ID NO 17: Mouse CDS mature Cometin
SEQ ID NO 18: Rat CDS mature Cometin
SEQ ID NO 19: Bovine Cometin protein (incl. signal peptide)
SEQ ID NO 20: Chicken Cometin protein (incl. signal peptide)
SEQ ID NO 21: Frog Cometin protein (incl. signal peptide)
SEQ ID NO 22: Zebrafish Cometin protein (incl. signal peptide)
SEQ ID NO 23: Human METRN protein (incl. signal peptide)
SEQ ID NO 24: Mouse METRN protein (incl. signal peptide)
SEQ ID NO 25: Rat METRN protein (incl. signal peptide)

SEQ ID NO 1: Human Cometin cDNA(NM_001004431.1)
```
   1 gcggggggcg cgcgacgtga ccaccggac tcgaagcccg ccccgccccc
  51 gcccggctcg ccggctccgg ggtctgctcc ggggtcgcg gacgcgggc
 101 cgggcggcgg agccggcgcc agagcatgcg gggcgcggcg cgggcggcct
 151 ggggcgcgc ggggcagccg tggccgcgac ccccgcccc gggcccgccc
 201 ccgccgccgc tcccgctgct gctcctgctc ctggccgggc tgctgggcgg
 251 cgcgggcgcg cagtactcca gcgaccggtg cagctggaag gggagcgggc
 301 tgacgcacga ggcacacagg aaggaggtgg agcaggtgta tctgcgctgt
 351 gcggcgggtg ccgtggagtg gatgtaccca acaggtgctc tcatcgttaa
 401 cctgcggccc aacaccttct cgcctgcccg gcacctgacc gtgtgcatca
 451 ggtccttcac ggactcctcg ggggccaata tttatttgga aaaaactgga
 501 gaactgagac tgctggtacc ggacggggac ggcaggcccg gccgggtgca
 551 gtgttttggc ctggagcagg gcggcctgtt cgtggaggcc acgccgcagc
 601 aggatatcgg ccggaggacc acaggcttcc agtacgagct ggttaggagg
 651 cacagggcgt cggacctgca cgagctgtct gcgccgtgcc gtccctgcag
 701 tgacaccgag gtgctcctag ccgtctgcac cagcgacttc gccgttcgag
 751 gctccatcca gcaagttacc cacgagcctg agcggcagga ctcagccatc
 801 cacctgcgcg tgagcagact ctatcggcag aaaagcaggg tcttcgagcc
 851 ggtgcccgag ggtgacggcc actggcaggg gcgcgtcagg acgctgctgg
 901 agtgtggcgt gcggccgggg catggcgact cctcttcac tggccacatg
 951 cacttcgggg aggcgcggct cggctgtgcc ccacgcttca aggacttcca
1001 gaggatgtac agggatgccc aggagagggg gctgaaccct tgtgaggttg
1051 gcacggactg actccgtggg ccgctgccct tcctctcctg atgagtcaca
1101 ggctgcgtg ggcgctgcgg tcctggtggg gccgtgcggt gagggccgcg
1151 cgctgggagc cgcatgccct gggcccaggc ctgaccctgg taccgaagct
1201 gtggacgttc tcgccacact caaccccatg agcttccagc aaggatgcc
1251 ctggccgatt ggaaatgctg taaatgcaa actaagttat tatatttttt
1301 tttggtaaaa aagaaatgtc cataggaaac aaaaaaaaaa aaaaaaa
                    ORF in bold
```

SEQ ID NO 2: Human Cometin protein (NP_001004431.1)
```
   1 mrgaaraawg ragqpwprpp apgpppplp llllllagll ggagaqyssd
  51 rcswkgsglt heahrkeveq vylrcaagav ewmyptgali vnlrpntfsp
 101 arhltvcirs ftdssganiy lektgelrll vpdgdgrpgr vqcfgleqgg
 151 lfveatpqqd igrrttgfqy elvrrhrasd lhelsapcrp csdtevllav
 201 ctsdfavrgs iqqvtheper qdsaihlrvs rlyrqksrvf epvpegdghw
 251 qgrvrtllec gvrpghgdfl ftghmhfgea rlgcaprfkd fqrmyrdaqe
 301 rglnpcevgt d
```

SEQ ID NO 3: Mouse Cometin cDNA (NM_144797.3)
```
   1 agaggttcta ggggcagccg gcgcgcttct ctagttgcag cttgggcggc
  51 tcctgtggtg ggcggctagg ggcgagccgg gatgggctat agacgcgcga
 101 cgtgatcagt tcgcacgcgg acccacgcct cccatcgctc tgcctcaaga
 151 gcctattctg tgggtgcagg cacgcaccgg acgcagaccc ggccggagca
 201 tgcggggtgc ggtgtgggcg gccggaggc gcgcggggca gcagtggcct
```

-continued

```
 251   cggtccccgg gccctgggcc gggtccgccc ccgccgccac cgctgctgtt
 301   gctgctacta ctgctgctgg gcggcgcgag cgctcagtac tccagcgacc
 351   tgtgcagctg aaggggagt gggctcaccc gagaggcacg cagcaaggag
 401   gtggagcagg tgtacctgcg ctgctccgca ggctctgtgg agtggatgta
 451   cccaactggg gcgctcattg ttaacctacg gcccaacacc ttctcacctg
 501   cccagaactt gactgtgtgc atcaagcctt cagggactc ctctggagcc
 551   aatatttatt tggaaaaaac tggagaacta agactgttgg tgcgggacat
 601   cagaggtgag cctggccaag tgcagtgctt cagcctggag cagggaggct
 651   tatttgtgga ggcgacaccc caacaggaca tcagcagaag gaccacaggc
 701   ttccagtatg agctgatgag tgggcagagg ggactggacc tgcacgtgct
 751   gtctgccccc tgtcggcctt gcagtgacac tgaggtcctc cttgccatct
 801   gtaccagtga ctttgttgtc cgaggcttca ttgaggacgt cacacatgta
 851   ccagaacagc aagtgtcagt catctacctg cgggtgaaca ggcttcacag
 901   gcagaagagc agggtcttcc agccagctcc tgaggacagt ggccactggc
 951   tgggccatgt cacaacactg ctgcagtgtg gagtacgacc agggcatggg
1001   gaattcctct tcactggaca tgtgcacttt ggggaggcac aacttggatg
1051   tgccccacgc tttagtgact ttcaaaggat gtacaggaaa gcagaagaaa
1101   tgggcataaa ccctgtgaa atcaatatgg agtgacttgc agggtgacac
1151   agtactgttg tccttcagat gagccatgtt ttgtgggctc agtcgctcta
1201   tcatatcctg atagagattg cagactggtg gcatgggccc agcctggtgc
1251   tagaactggg aaggtacatg ctgctctgac cccttaggtc ccagccaagg
1301   atgccctgac ccattggaac tgctgtaaaa tgcaaactaa gttattatat
1351   ttttttttgta aaagatgcct tggtgtgcca tttaatagtg ttttttacaaa
1401   gttattttca ggcattggat ttggcctggt atattggtgg gagctaggtt
1451   atggtgtgca gtgatggcta tggctcagcc ttgttattcc tgtgatggaa
1501   atgtatggag caaatacttt ctaatttccc cttcattta ttttctattt
1551   taaaagacca tctttgccgt tgagaacctt tccagactgt atggaggctg
1601   ctcccattcc agggagtaaa gaccaggatc tgagactagt attacatcca
1651   tcttaaccca tcagatgggt acctgcattg aaccttctct gctcagctat
1701   ggcctgctgt cccaaagacc ttttgctctc tggacagttc cagatggtgc
1751   tgcctggctt aagggacttg ttcctccctt gctcctacca ggccactgtt
1801   gctttctgca tctgtcccac tgaaccagtc ttgtcctttg accctgagtt
1851   tccccaaatg cacacatcaa atccctgaat accaagggac taacctactt
1901   aatggcccat ttcttcagag ggtgtgggtt ttccctatag taagaaaatc
1951   tccacaagtt gaagcttaaa cagtaggctt tcgttcatac agtcctggaa
2001   gccagaatgg gtgtgagcag aatcacattt cctccggaga ctccaggagg
2051   gactttatag cttctggtga ctccaggaat ccttggcttg taacaatttc
2101   actctggcat tgctttccct gccatgtgac ttctgccttg tatgtgaggg
2151   cctgtatcaa atctctgtct tgggaggata cagatcattg acttagggcc
2201   cactccggtg acctcacctt cacctgaaat ttactcgatt tccatttagg
2251   tcagaggcaa aggctacaaa aaatatcaaa tccggagaaa gattcaatgg
```

-continued

```
2301 ttaggcactt gctactctta caaaggacct gtgttcgatt cccatgttgg 2351 gaactcatgt taggtggctt aaaattgcct ataactacaa ttccagggga 2401 tctagcaacc tcttctcgcc acacacaagc acacacacac acacacacac 2451 acacacacaa ttaaaaac
ORF in bold
```

SEQ ID NO 4: Mouse Cometin protein (NP_659046.1)

```
  1 mrgavwaarr ragqqwprsp gpgpgppppp pllllllll ggasaqyssd 51 lcswkgsglt rearskeveq vylrcsagsv ewmyptgali vnlrpntfsp 101 aqnltvcikp frdssganiy lektgelrll vrdirgepgq vqcfsleqgg 151 lfveatpqqd isrrttgfqy elmsgqrgld lhvlsapcrp csdtevllai 201 ctsdfvvrgf iedvthvpeq qvsviylrvn rlhrqksrvf qpapedsghw 251 lghvttllqc gvrpghgefl ftghvhfgea qlgcaprfsd fqrmyrkaee 301 mginpceinm e
```

SEQ ID NO 5: Rat Cometin cDNA (NM_001014104.1)

```
   1 ggcagccggc gcgcttctct ggttgcagct tgggcggctg gggcggctcc 51 tatggtgggc ggccagggcc tagacgggat ggcctgtaga cgcgcgacgt 101 gatcagctcg cacgcggacc cacgcctccc gcagcactgc ctcaacagtc 151 tattctgtgg gtgcaggcac gcaccggtct cagaccctgc cggagcatgc 201 ggggtgtggt gtgggcggcc cggaggcgcg cggggcagca gtggcctcgg 251 tccccggggcc ctgggccggg tccgcccccg ccgccaccgc tgctgttgct 301 gctactgctg ctgctgggcg gcgcgagcgc gcagtactcc agcgacctgt 351 gcagctggaa ggggagtggg ctcacccggg aggcacacag caaggaggtg 401 gagcaggtgt acctgcgctg ctcagcaggc tctgtggaat ggatgtaccc 451 aaccggggcg ctcattgtta acctacgcc caacaccttc tcacctgccc 501 agaacttgac tgtgtgcatc aagcctttca gggactcctc tgggggccaat 551 atttatttgg aaaaaactgg agaactaaga ctgttggtgc gggatgtcag 601 aggcgaacct ggccaagtgc agtgcttcag cctagagcag ggaggcttat 651 ttgtggaggc cacaccccag caggacatca gcagaaggac acaggcttc 701 cagtatgagc tgatgagtgg cagaggggga ctggacctgc acgtgctctc 751 tgcccctgt cgaccttgca gcgacactga ggtcctcctt gccatctgca 801 ccagtgactt tgttgtccga ggcttcatcg aggatgtcac ccatgtacca 851 gaacagcaag tgtcagtcat tcacctacgg gtgagcaggc tccacaggca 901 gaagagcagg gtcttccagc cagctcctga ggacagtggc cactggctgg 951 gccatgtcac aacactgttg cagtgtggag tacgaccagg gcatggagaa 1001 ttcctcttca ctggacatgt gcactttggg gaggcacaac ttggatgtgc 1051 cccacgcttt agtgactttc aaaagatgta caggaaagca gaagaaaggg 1101 gcataaaccc ttgtgaaata aatatggagt gacttgcagg gtgacaccgt 1151 actgctgtcc ttcagatgag ccatggctca gttgctctat caaatcccga 1201 tagagattgc agactggtgg catgagcccc gcctggtgct tgaactggga 1251 agggaggtac atgctgctct gaccccttag gtcccattca aggatgccct 1301 gacccattgg aaatgttgta aatgcaaac taagttatta tattttttt 1351 gtaaaagaaa aaaaaaaaaa aaaaaaaaa
ORF in bold
```

SEQ ID NO 6: Rat Cometin protein (NP_001014126)
```
  1  mrgvvwaarr ragqqwprsp gpgpgppppp pllllllll  ggasaqyssd 51  lcswkgsglt reahskeveq vylrcsagsv ewmyptgall vnlrpntfsp 101  aqnitvcikp frdssganly lektgelrll vrdvrgepgq vqcfsleqgg 151  lfveatpqqd isrrttgfqy elmsgqrgld lhvlsapcrp csdtevllai 201  ctsdfvvrgf ledvthvpeq qvsvihlrvs rlhrqksrvf qpapedsghw 251  lghvttllqc gvrpghgefl ftghvhfgea qlgcaprfsd fqkmyrkaee 301  rginpceinm e
```

SEQ ID NO 7: human mature Cometin protein
```
QYSSDRCSWK GSGLTHEAHR KEVEQVYLRC AAGAVEWMYP TGALIVNLRP NTFSPARHLT   60

VCIRSFTDSS GANIYLEKTG ELRLLVPDGD GRPGRVQCFG LEQGGLFVEA TPQQDIGRRT  120

TGFQYELVRR HRASDLHELS APCRPCSDTE VLLAVCTSDF AVRGSIQQVT HEPERQDSAI  180

HLRVSRLYRQ KSRVFEPVPE GDGHWQGRVR TLLECGVRPG HGDFLFTGHM HFGEARLGCA  240

PRFKDFQRMY RDAQERGLNP CEVGTD                                      266
```

SEQ ID NO 8: mouse mature Cometin protein
```
QYSSDLCSWK GSGLTREARS KEVEQVYLRC SAGSVEWMYP TGALIVNLRP NTFSPAQNLT   60

VCIKPFRDSS GANIYLEKTG ELRLLVRDIR GEPGQVQCFS LEQGGLFVEA TPQQDISRRT  120

TGFQYELMSG QRGLDLHVLS APCRPCSDTE VLLAICTSDF VVRGFIEDVT HVPEQQVSVI  180

YLRVNRLHRQ KSRVFQPAPE DSGHWLGHVT TLLQCGVRPG HGEFLFTGHV HFGEAQLGCA  240

PRFSDFQRMY RKAEEMGINP CEINME                                      266
```

SEQ ID NO 9: rat mature Cometin protein
```
QYSSDLCSWK GSGLTREAHS KEVEQVYLRC SAGSVEWMYP TGALIVNLRP NTFSPAQNLT   60

VCIKPFRDSS GANIYLEKTG ELRLLVRDVR GEPGQVQCFS LEQGGLFVEA TPQQDISRRT  120

TGFQYELMSG QRGLDLHVLS APCRPCSDTE VLLAICTSDF VVRGFIEDVT HVPEQQVSVI  180

HLRVSRLHRQ KSRVFQPAPE DSGHWLGHVT TLLQCGVRPG HGEFLFTGHV HFGEAQLGCA  240

PRFSDFQKMY RKAEERGINP CEINME                                      266
```

SEQ ID NO 10: human Cometin core fragment
```
CSWKGSGLTH EAHRKEVEQV YLRCAAGAVE WMYPTGALIV NLRPNTFSPA RHLTVCIRSF   60

TDSSGANIYL EKTGELRLLV PDGDGRPGRV QCFGLEQGGL FVEATPQQDI GRRTTGFQYE  120

LVRRHRASDL HELSAPCRPC SDTEVLLAVC TSDFAVRGSI QQVTHEPERQ DSAIHLRVSR  180

LYRQKSRVFE PVPEGDGHWQ GRVRTLLECG VRPGHGDFLF TGHMHFGEAR LGCAPRFKDF  240

QRMYRDAQER GLNPC                                                  255
```

SEQ ID NO 11: mouse Cometin core fragment
```
CSWKGSGLTR EARSKEVEQV YLRCSAGSVE WMYPTGALIV NLRPNTFSPA QNLTVCIKPF   60

RDSSGANIYL EKTGELRLLV RDIRGEPGQV QCFSLEQGGL FVEATPQQDI SRRTTGFQYE  120

LMSGQRGLDL HVLSAPCRPC SDTEVLLAIC TSDFVVRGFI EDVTHVPEQQ VSVIYLRVNR  180

LHRQKSRVFQ PAPEDSGHWL GHVTTLLQCG VRPGHGEFLF TGHVHFGEAQ LGCAPRFSDF  240

QRMYRKAEEM GINPC                                                  255
```

SEQ ID NO 12: rat Cometin core fragment
```
CSWKGSGLTR EAHSKEVEQV YLRCSAGSVE WMYPTGALIV NLRPNTFSPA QNLTVCIKPF   60

RDSSGANIYL EKTGELRLLV RDVRGEPGQV QCFSLEQGGL FVEATPQQDI SRRTTGFQYE  120

LMSGQRGLDL HVLSAPCRPC SDTEVLLAIC TSDFVVRGFI EDVTHVPEQQ VSVIHLRVSR  180

LHRQKSRVFQ PAPEDSGHWL GHVTTLLQCG VRPGHGEFLF TGHVHFGEAQ LGCAPRFSDF  240

QKMYRKAEER GINPC                                                  255
```

SEQ ID NO 13, human Cometin ORF
```
atgcggggcg cggcgcgggc ggcctggggg cgcgcggggc agccgtggcc gcgaccccc    60
gccccgggcc cgccccgcc  gccgctcccg ctgctgctcc tgctcctggc cgggctgctg  120
ggcggcgcgg gcgcgcagta ctccagcgac cggtgcagct ggaaggggag cgggctgacg  180
cacgaggcac acaggaagga ggtggagcag gtgtatctgc gctgtgcggc gggtgccgtg  240
gagtggatgt acccaacagg tgctctcatc gttaacctgc ggcccaacac cttctcgcct  300
gccccggcacc tgaccgtgtg catcaggtcc ttcacggact cctcggggc  caatatttat  360
ttggaaaaaa ctggagaact gagactgctg gtaccggacg ggacggcag  gcccggccgg  420
gtgcagtgtt ttggcctgga gcagggcggc ctgttcgtgg aggccacgcc gcagcaggat  480
atcggccgga ggaccacagg cttccagtac gagctggtta ggaggcacag ggcgtcggac  540
ctgcacgagc tgtctgcgcc gtgccgtccc tgcagtgaca ccgaggtgct cctagccgtc  600
tgcaccagcg acttcgccgt cgaggctcc  atccagcaag ttacccacga gcctgagcgg  660
caggactcag ccatccacct gcgcgtgagc agactctatc ggcagaaaag cagggtcttc  720
gagccggtgc ccgagggtga cggccactgg caggggcgcg tcaggacgct gctggagtgt  780
ggcgtgcggc cggggcatgg cgacttcctc ttcactggcc acatgcactt cggggaggcg  840
cggctcggct gtgccccacg cttcaaggac ttccagagga tgtacaggga tgcccaggag  900
agggggctga accccttgtga ggttggcacg gactga                           936
```
SEQ ID No 14, mouse Cometin ORF
```
atgcggggtg cggtgtgggc ggcccggagg cgcgcggggc agcagtggcc tcggtccccg   60
ggccctgggc cgggtccgcc cccgccgcca ccgctgctgt tgctgctact actgctgctg  120
ggcggcgcga gcgctcagta ctccagcgac ctgtgcagct ggaaggggag tgggctcacc  180
cgagaggcac gcagcaagga ggtggagcag gtgtacctgc gctgctccgc aggctctgtg  240
gagtggatgt acccaactgg ggcgctcatt gttaacctac ggcccaacac cttctcacct  300
gcccagaact tgactgtgtg catcaagcct ttcaggact  cctctggagc caatatttat  360
ttggaaaaaa ctggagaact aagactgttg gtgcgggaca tcagaggtga gcctggccaa  420
gtgcagtgct tcagcctgga gcagggaggc ttatttgtgg aggcgacacc ccaacaggac  480
atcagcagaa ggaccacagg cttccagtat gagctgatga gtgggcagag gggactggac  540
ctgcacgtgc tgtctgcccc ctgtcggcct tgcagtgaca ctgaggtcct ccttgccatc  600
tgtaccagtg actttgttgt ccgaggcttc attgaggacg tcacacatgt accagaacag  660
caagtgtcag tcatctacct gcgggtgaac aggcttcaca ggcagaagag cagggtcttc  720
cagccagctc ctgaggacag tggccactgg ctgggccatg tcacaacact gctgcagtgt  780
ggagtacgac cagggcatgg ggaattcctc ttcactggac atgtgcactt ggggaggca  840
caacttggat gtgccccacg ctttagtgac tttcaaagga tgtacaggaa agcagaagaa  900
atgggcataa acccctgtga aatcaatatg gagtga                            936
```
SEQ ID NO 15, rat Cometin ORF
```
atgcggggtg tggtgtgggc ggcccggagg cgcgcggggc agcagtggcc tcggtccccg   60
ggccctgggc cgggtccgcc cccgccgcca ccgctgctgt tgctgctact gctgctgctg  120
ggcggcgcga gcgcgcagta ctccagcgac ctgtgcagct ggaaggggag tgggctcacc  180
cgggaggcac acagcaagga ggtggagcag gtgtacctgc gctgctcagc aggctctgtg  240
gaatggatgt acccaaccgg ggcgctcatt gttaacctac ggcccaacac cttctcacct  300
gcccagaact tgactgtgtg catcaagcct ttcaggact  cctctggggc caatatttat  360
ttggaaaaaa ctggagaact aagactgttg gtgcgggatg tcagaggcga acctggccaa  420
```

```
gtgcagtgct tcagcctaga gcagggaggc ttatttgtgg aggccacacc ccagcaggac    480
atcagcagaa ggaccacagg cttccagtat gagctgatga gtgggcagag gggactggac    540
ctgcacgtgc tctctgcccc ctgtcgacct tgcagcgaca ctgaggtcct ccttgccatc    600
tgcaccagtg actttgttgt ccgaggcttc atcgaggatg tcacccatgt accagaacag    660
caagtgtcag tcattcacct acgggtgagc aggctccaca ggcagaagag cagggtcttc    720
cagccagctc ctgaggacag tggccactgg ctgggccatg tcacaacact gttgcagtgt    780
ggagtacgac cagggcatgg agaattcctc ttcactggac atgtgcactt tggggaggca    840
caacttggat gtgccccacg ctttagtgac tttcaaaaga tgtacaggaa agcagaagaa    900
aggggcataa acccttgtga aataaatatg gagtga                              936

SEQ ID NO 16, Human CDS mature Cometin
cagtactcca gcgaccggtg cagctggaag gggagcgggc tgacgcacga ggcacacagg     60
aaggaggtgg agcaggtgta tctgcgctgt gcggcgggtg ccgtggagtg gatgtaccca    120
acaggtgctc tcatcgttaa cctgcggccc aacaccttct cgcctgcccg gcacctgacc    180
gtgtgcatca ggtccttcac ggactcctcg ggggccaata tttatttgga aaaaactgga    240
gaactgagac tgctggtacc ggacggggac ggcaggcccg gccgggtgca gtgttttggc    300
ctggagcagg gcggcctgtt cgtggaggcc acgccgcagc aggatatcgg ccggaggacc    360
acaggcttcc agtacgagct ggttaggagg cacagggcgt cggacctgca cgagctgtct    420
gcgccgtgcc gtccctgcag tgacaccgag gtgctcctag ccgtctgcac cagcgacttc    480
gccgttcgag gctccatcca gcaagttacc cacgagcctg agcggcagga ctcagccatc    540
cacctgcgcg tgagcagact ctatcggcag aaaagcaggg tcttcgagcc ggtgcccgag    600
ggtgacggcc actggcaggg gcgcgtcagg acgctgctgg agtgtggcgt gcggccgggg    660
catggcgact tcctcttcac tggccacatg cacttcgggg aggcgcggct cggctgtgcc    720
ccacgcttca aggacttcca gaggatgtac agggatgccc aggagagggg gctgaaccct    780
tgtgaggttg gcacggactg a                                              801

SEQ ID NO 17, Mouse CDS mature Cometin
cagtactcca gcgacctgtg cagctggaag gggagtgggc tcacccgaga ggcacgcagc     60
aaggaggtgg agcaggtgta cctgcgctgc tccgcaggct ctgtggagtg gatgtaccca    120 actgggcgc tcattgttaa cctacggccc aacaccttct cacctgccca gaacttgact    180
gtgtgcatca agcctttcag ggactcctct ggagccaata tttatttgga aaaaactgga    240
gaactaagac tgttggtgcg ggacatcaga ggtgagcctg gccaagtgca gtgcttcagc    300
ctggagcagg gaggcttatt tgtggaggcg acaccccaac aggacatcag cagaaggacc    360
acaggcttcc agtatgagct gatgagtggg cagaggggac tggacctgca cgtgctgtct    420 gcccctgtc ggccttgcag tgacactgag gtcctccttg ccatctgtac cagtgacttt    480
gttgtccgag gcttcattga ggacgtcaca catgtaccag aacagcaagt gtcagtcatc    540
tacctgcggg tgaacaggct tcacaggcag aagagcaggg tcttccagcc agctcctgag    600
gacagtggcc actggctggg ccatgtcaca acactgctgc agtgtggagt acgaccaggg    660
catggggaat tcctcttcac tggacatgtg cactttgggg aggcacaact tggatgtgcc    720
ccacgcttta gtgactttca aggatgtac aggaaagcag aagaatggg cataaacccc      780 tgtgaaatca atatggagtg a                                              801

SEQ ID NO 18, Rat CDS mature Cometin
cagtactcca gcgacctgtg cagctggaag gggagtgggc tcacccggga ggcacacagc     60
aaggaggtgg agcaggtgta cctgcgctgc tcagcaggct ctgtggaatg gatgtaccca    120
```

```
-continued
accggggcgc tcattgttaa cctacggccc aacaccttct cacctgccca gaacttgact    180
gtgtgcatca agccttttcag ggactcctct ggggccaata tttatttgga aaaaactgga   240
gaactaagac tgttggtgcg ggatgtcaga ggcgaacctg gccaagtgca gtgcttcagc    300
ctagagcagg gaggcttatt tgtggaggcc acacccagc aggacatcag cagaaggacc     360
acaggcttcc agtatgagct gatgagtggg cagaggggac tggacctgca cgtgctctct    420
gccccctgtc gaccttgcag cgacactgag gtcctccttg ccatctgcac cagtgacttt    480
gttgtccgag gcttcatcga ggatgtcacc catgtaccag aacagcaagt gtcagtcatt    540
cacctacggg tgagcaggct ccacaggcag aagagcaggg tcttccagcc agctcctgag    600
gacagtggcc actggctggg ccatgtcaca acactgttgc agtgtggagt acgaccaggg    660
catggagaat tcctcttcac tggacatgtg cactttgggg aggcacaact tggatgtgcc    720
ccacgcttta gtgactttca aaagatgtac aggaaagcag aagaaagggg cataaaccct    780
tgtgaaataa atatggagtg a                                              801
```

Example 2

Production of recombinant Cometin. Mouse Cometin (mCometin, Accession # NP_659046) (aa46-311 with a signal peptide from hCD33) was cloned into a mammalian expression vector. The vector was transfected into the CHO, Chinese Hamster Ovary, cell line by electroporation. Stable clones were isolated and screened for expression of mCometin by Western blotting using a custom made monoclonal antibody. Conditioned medium from cultures containing mCometin was supplemented with 20 mM MOPS, the pH was adjusted to 6.5, and filtered through a 0.2 um filter. The sample was applied to an anion exchange chromatography resin, equilibrated in 20 mM MOPS (3-(N-morpholino) propanesulfonic acid), 0.1 M NaCl, pH 6.5. The fractions containing mCometin were supplemented with 2 M NaCl, the pH was adjusted to 7.0, and then applied to a phenyl sepharose resin. Bound proteins were eluted with a decreasing gradient of NaCl. Fractions enriched in mCometin were pooled and dialyzed in 20 mM Tris, pH 7.8. This sample was applied to an anion exchange chromatography resin equilibrated in the same buffer. Bound proteins were eluted with an increasing gradient of NaCl. Fractions containing mCometin were pooled, concentrated and loaded onto a Superdex gel filtration column and then equilibrated in PBS. mCometin eluted as an approximately 30 kDa molecular weight protein. Fractions of interest were pooled, concentrated, dialyzed against PBS and stored at −80° C.

Example 3

Animal Experiments

Surgery. Male Sprague-Dawley rats (Harlan, The Netherlands) weighing 380-450 g were fitted with a chronic intrathecal catheter with the tip at the lumbar enlargement (Storkson et al., 1996). Three to five days after catheter implantation, ischemic sciatic nerve injury was produced using a photochemical method (Kupers et al., 1998). Briefly, under general anesthesia (chloral hydrate 300 mg/kg), the left sciatic nerve was exposed at mid-thigh level and irradiated for 1.5 min with an argon laser operating at 514 nm at an average power of 0.17 W. Erythrosin B (32.5 mg/kg dissolved in 0.9% saline) was injected intravenously through the tail vein just prior to irradiation. This operation leads to a highly reproducible allodynia, which may be characterised as hypersensitivity, within 7 days.

Evaluation of Allodynia. For evaluation of mechanical allodynia, a set of calibrated nylon monofilaments (von Frey hairs, Stoelting, I L) was applied to the glabrous skin of the paws with increasing force until the animal withdraws the limb. Each monofilament was applied 5 times and withdrawal threshold was determined as the force at which the animal withdraws the paw from at least 3 out of 5 consecutive stimuli. The response to cold was tested with ethyl chloride, which was briefly (<1 s) sprayed on the plantar surface of the hind paw. The response was scored as the following: 0=no response, 1=startle-like response, no hindpaw withdrawal (normal), 2=brief withdrawal of the stimulated hindpaw (mild pain), 3=sustained or repeated withdrawal of the stimulated hindpaw, brief licking or shaking (severe pain). All tests were performed by an experimenter who was blind with respect to the experimental conditions. After every testing session, the body weight of the animals was measured to the nearest gram.

Experimental Setup. Baseline responses were evaluated after catheter implantation and again before sciatic nerve irradiation. Rats that developed allodynia to mechanical and cold stimulation 7 days after nerve injury were randomly divided into two groups (N=8) which were given vehicle or 6 μg recombinant Cometin at a volume of 10 μl intrathecally. Each rat received six injections over a two week period (on day 7, 9, 11, 14, 16 and 18 counting from the time of nerve injury). Behavioral testing was conducted prior to intrathecal injection on respective treatment days and furthermore on days 21, 25, 28 and 35 following treatment cessation.

Results

As seen in FIG. 4, the baseline paw withdrawal threshold to mechanical stimulation was 51.5±5.7 g. 7 days after photochemically induced sciatic nerve injury, rats developed significant mechanical allodynia evident as a reduced paw withdrawal threshold of approximately 8 g. Rats were then randomly divided into two groups subsequently receiving either vehicle or Cometin as six intrathecal injections in the space of two weeks. It is clear that intrathecal injection of Cometin significantly reduced mechanical allodynia (FIG. 4). The mechanical allodynia was gradually reestablished within a week after treatment cessation. Intrathecal injection of vehicle did not affect the mechanical allodynia throughout the experiment.

As seen in FIG. 5, the baseline cold response is 1 corresponding to a normal startle-like response. 7 days after photochemically induced sciatic nerve injury, rats developed a marked cold allodynia evident as a mild pain reaction. Treatment with Cometin quickly reversed the cold allodynia and animals had a near normal response to cold in the treatment period. A significantly positive effect of Cometin was also observed three days after treatment cessation. However, cold allodynia was fully reestablished a week after the treatment ended. Vehicle had no effect on cold allodynia.

No reduction in body weight (FIG. 6) or other adverse effects was observed in the study.

CONCLUSION

Repeated intrathecal injection of Cometin significantly reduces mechanical and cold allodynia in rats after sciatic nerve injury. No immediate adverse effects of the treatment were observed.

REFERENCES

Kupers, R., Yu, W., Persson, J. K., Xu, X. J., and Wiesenfeld-Hallin, Z. (1998). Photochemically-induced ischemia of the rat sciatic nerve produces a dose-dependent and highly reproducible mechanical, heat and cold allodynia, and signs of spontaneous pain. Pain 76, 45-59.

Storkson, R. V., Kjorsvik, A., Tjolsen, A., and Hole, K. (1996). Lumbar catheterization of the spinal subarachnoid space in the rat. J. Neurosci. Methods 65, 167-172.

The invention claimed is:

1. A method of treatment of hyperalgesia, spontaneous pain, or phantom pain in a subject in need thereof, comprising administering to said subject a therapeutically effective amount of a neurotrophic polypeptide comprising an amino acid sequence that is at least 90% identical to SEQ ID NO:7.

2. The method according to claim 1, wherein said subject is diagnosed with painful diabetic neuropathy, post-herpatic neuralgia or sciatica.

3. The method according to claim 1, wherein said hyperalgesia is thermal hyperalgesia.

4. The method according to claim 3, wherein said hyperalgesia is cold hyperalgesia.

5. The method according to claim 1, wherein said hyperalgesia is mechanical hyperalgesia.

6. The method according to claim 1, wherein the subject does not experience weight loss during treatment.

7. The method according to claim 1, wherein the subject is human.

8. The method according to claim 1, wherein the polypeptide is administered systemically.

9. The method according to claim 1, wherein the polypeptide is administered by subcutaneous injection or intrathecal administration.

10. The method according to claim 1, wherein the treatment is administered in dosages of 1 µg/kg -10,000 µg/kg body weight.

11. The method according to claim 1, wherein said administration is repeated daily.

12. The method according to claim 1, wherein said administration is repeated at least 1-3 times weekly.

13. The method according to claim 1, wherein the polypeptide comprises an amino acid sequence that is at least 95% identical to SEQ ID NO:7.

14. The method according to claim 1, wherein the polypeptide comprises the amino acid sequence of SEQ ID NO:7.

* * * * *

SEQUENCE LISTING

```
<160> NUMBER OF SEQ ID NOS: 25

<210> SEQ ID NO 1
<211> LENGTH: 1348
<212> TYPE: DNA
<213> ORGANISM: Homo sapiens
<220> FEATURE:
<221> NAME/KEY: CDS
<222> LOCATION: (126)..(1061)

<400> SEQUENCE: 1 gcgggggcg cgcgacgtga ccacccggac tcgaagcccg ccccgccccc gcccggctcg      60
ccggctccgg ggtctgctcc gggggtcgcg gacgcggggc cgggcggcgg agccggcgcc     120 agagc atg cgg ggc gcg gcg cgg gcg gcc tgg ggg cgc gcg ggg cag ccg    170
      Met Arg Gly Ala Ala Arg Ala Ala Trp Gly Arg Ala Gly Gln Pro
       1               5                  10                  15 tgg ccg cga ccc ccc gcc ccg ggc ccg ccc ccg ccg ccg ctc ccg ctg      218
Trp Pro Arg Pro Pro Ala Pro Gly Pro Pro Pro Pro Pro Leu Pro Leu
                20                  25                  30 ctg ctc ctg ctc ctg gcc ggg ctg ctg ggc ggc gcg ggc gcg cag tac      266
Leu Leu Leu Leu Leu Ala Gly Leu Leu Gly Gly Ala Gly Ala Gln Tyr
            35                  40                  45 tcc agc gac cgg tgc agc tgg aag ggg agc ggg ctg acg cac gag gca      314
Ser Ser Asp Arg Cys Ser Trp Lys Gly Ser Gly Leu Thr His Glu Ala
         50                  55                  60 cac agg aag gag gtg gag cag gtg tat ctg cgc tgt gcg gcg ggt gcc      362
His Arg Lys Glu Val Glu Gln Val Tyr Leu Arg Cys Ala Ala Gly Ala
     65                  70                  75 gtg gag tgg atg tac cca aca ggt gct ctc atc gtt aac ctg cgg ccc      410
Val Glu Trp Met Tyr Pro Thr Gly Ala Leu Ile Val Asn Leu Arg Pro
 80                  85                  90                  95 aac acc ttc tcg cct gcc cgg cac ctg acc gtg tgc atc agg tcc ttc      458
Asn Thr Phe Ser Pro Ala Arg His Leu Thr Val Cys Ile Arg Ser Phe
                100                 105                 110 acg gac tcc tcg ggg gcc aat att tat ttg gaa aaa act gga gaa ctg      506
Thr Asp Ser Ser Gly Ala Asn Ile Tyr Leu Glu Lys Thr Gly Glu Leu
            115                 120                 125 aga ctg ctg gta ccg gac ggg gac ggc agg ccc ggc cgg gtg cag tgt      554
Arg Leu Leu Val Pro Asp Gly Asp Gly Arg Pro Gly Arg Val Gln Cys
        130                 135                 140 ttt ggc ctg gag cag ggc ggc ctg ttc gtg gag gcc acg ccg cag cag      602
Phe Gly Leu Glu Gln Gly Gly Leu Phe Val Glu Ala Thr Pro Gln Gln
    145                 150                 155 gat atc ggc cgg agg acc aca ggc ttc cag tac gag ctg gtt agg agg      650
Asp Ile Gly Arg Arg Thr Thr Gly Phe Gln Tyr Glu Leu Val Arg Arg
160                 165                 170                 175 cac agg gcg tcg gac ctg cac gag ctg tct gcg ccg tgc cgt ccc tgc      698
His Arg Ala Ser Asp Leu His Glu Leu Ser Ala Pro Cys Arg Pro Cys
                180                 185                 190
```

-continued

```
agt gac acc gag gtg ctc cta gcc gtc tgc acc agc gac ttc gcc gtt    746
Ser Asp Thr Glu Val Leu Leu Ala Val Cys Thr Ser Asp Phe Ala Val
        195                 200                 205 cga ggc tcc atc cag caa gtt acc cac gag cct gag cgg cag gac tca    794
Arg Gly Ser Ile Gln Gln Val Thr His Glu Pro Glu Arg Gln Asp Ser
            210                 215                 220 gcc atc cac ctg cgc gtg agc aga ctc tat cgg cag aaa agc agg gtc    842
Ala Ile His Leu Arg Val Ser Arg Leu Tyr Arg Gln Lys Ser Arg Val
225                 230                 235 ttc gag ccg gtg ccc gag ggt gac ggc cac tgg cag ggg cgc gtc agg    890
Phe Glu Pro Val Pro Glu Gly Asp Gly His Trp Gln Gly Arg Val Arg
240                 245                 250                 255 acg ctg ctg gag tgt ggc gtg cgg ccg ggg cat ggc gac ttc ctc ttc    938
Thr Leu Leu Glu Cys Gly Val Arg Pro Gly His Gly Asp Phe Leu Phe
                260                 265                 270 act ggc cac atg cac ttc ggg gag gcg cgg ctc ggc tgt gcc cca cgc    986
Thr Gly His Met His Phe Gly Glu Ala Arg Leu Gly Cys Ala Pro Arg
            275                 280                 285 ttc aag gac ttc cag agg atg tac agg gat gcc cag gag agg ggg ctg   1034
Phe Lys Asp Phe Gln Arg Met Tyr Arg Asp Ala Gln Glu Arg Gly Leu
        290                 295                 300 aac cct tgt gag gtt ggc acg gac tga ctccgtgggc cgctgccctt         1081
Asn Pro Cys Glu Val Gly Thr Asp
        305                 310 cctctcctga tgagtcacag gctgcggtgg gcgctgcggt cctggtgggg ccgtgcggtg  1141
agggccgcgc gctgggagcc gcatgccctg ggcccaggcc tgaccctggt accgaagctg  1201
tggacgttct cgccacactc aaccccatga gcttccagcc aaggatgccc tggccgattg  1261
gaaatgctgt aaaatgcaaa ctaagttatt atattttttt ttggtaaaaa agaaatgtcc  1321
ataggaaaca aaaaaaaaaa aaaaaaa                                     1348
```

<210> SEQ ID NO 2
<211> LENGTH: 311
<212> TYPE: PRT
<213> ORGANISM: Homo sapiens

<400> SEQUENCE: 2

```
Met Arg Gly Ala Ala Arg Ala Ala Trp Gly Arg Ala Gly Gln Pro Trp
1               5                   10                  15

Pro Arg Pro Pro Ala Pro Gly Pro Pro Pro Pro Leu Pro Leu Leu
            20                  25                  30

Leu Leu Leu Leu Ala Gly Leu Leu Gly Gly Ala Gly Ala Gln Tyr Ser
        35                  40                  45

Ser Asp Arg Cys Ser Trp Lys Gly Ser Gly Leu Thr His Glu Ala His
    50                  55                  60

Arg Lys Glu Val Glu Gln Val Tyr Leu Arg Cys Ala Ala Gly Ala Val
65                  70                  75                  80

Glu Trp Met Tyr Pro Thr Gly Ala Leu Ile Val Asn Leu Arg Pro Asn
                85                  90                  95

Thr Phe Ser Pro Ala Arg His Leu Thr Val Cys Ile Arg Ser Phe Thr
            100                 105                 110

Asp Ser Ser Gly Ala Asn Ile Tyr Leu Glu Lys Thr Gly Glu Leu Arg
        115                 120                 125

Leu Leu Val Pro Asp Gly Asp Gly Arg Pro Gly Arg Val Gln Cys Phe
    130                 135                 140

Gly Leu Glu Gln Gly Gly Leu Phe Val Glu Ala Thr Pro Gln Gln Asp
145                 150                 155                 160
```

```
Ile Gly Arg Arg Thr Thr Gly Phe Gln Tyr Glu Leu Val Arg Arg His
                165                 170                 175

Arg Ala Ser Asp Leu His Glu Leu Ser Ala Pro Cys Arg Pro Cys Ser
            180                 185                 190

Asp Thr Glu Val Leu Leu Ala Val Cys Thr Ser Asp Phe Ala Val Arg
        195                 200                 205

Gly Ser Ile Gln Gln Val Thr His Glu Pro Glu Arg Gln Asp Ser Ala
    210                 215                 220

Ile His Leu Arg Val Ser Arg Leu Tyr Arg Gln Lys Ser Arg Val Phe
225                 230                 235                 240

Glu Pro Val Pro Glu Gly Asp Gly His Trp Gln Gly Arg Val Arg Thr
                245                 250                 255

Leu Leu Glu Cys Gly Val Arg Pro Gly His Gly Asp Phe Leu Phe Thr
            260                 265                 270

Gly His Met His Phe Gly Glu Ala Arg Leu Gly Cys Ala Pro Arg Phe
        275                 280                 285

Lys Asp Phe Gln Arg Met Tyr Arg Asp Ala Gln Glu Arg Gly Leu Asn
    290                 295                 300

Pro Cys Glu Val Gly Thr Asp
305                 310

<210> SEQ ID NO 3
<211> LENGTH: 2468
<212> TYPE: DNA
<213> ORGANISM: Mus musculus
<220> FEATURE:
<221> NAME/KEY: misc_feature
<222> LOCATION: (1)..(2468)
<223> OTHER INFORMATION: mMTRNL cDNA
<220> FEATURE:
<221> NAME/KEY: CDS
<222> LOCATION: (200)..(1135)

<400> SEQUENCE: 3
agaggttcta ggggcagccg gcgcgcttct ctagttgcag cttgggcggc tcctgtggtg      60
ggcggctagg ggcgagccgg gatgggctat agacgcgcga cgtgatcagt tcgcacgcgg     120
acccacgcct cccatcgctc tgcctcaaga gccattctg tgggtgcagg cacgcaccgg      180
```

| | | | | | | | | | | | | | | | | |
|---|---|---|---|---|---|---|---|---|---|---|---|---|---|---|---|---|
| acgcagaccc ggccggagc | atg | cgg | ggt | gcg | gtg | tgg | gcg | gcc | cgg | agg | cgc | | | | | 232 |
| | Met | Arg | Gly | Ala | Val | Trp | Ala | Ala | Arg | Arg | Arg | | | | | |
| | 1 | | | 5 | | | | | | 10 | | | | | | |
| gcg | ggg | cag | cag | tgg | cct | cgg | tcc | ccg | ggc | cct | ggg | ccg | ggt | ccg | ccc | 280 |
| Ala | Gly | Gln | Gln | Trp | Pro | Arg | Ser | Pro | Gly | Pro | Gly | Pro | Gly | Pro | Pro | |
| | 15 | | | | | 20 | | | | | 25 | | | | | |
| ccg | ccg | cca | ccg | ctg | ctg | ttg | ctg | cta | ctg | ctg | ctg | ggc | ggc | gcg | | 328 |
| Pro | Pro | Pro | Pro | Leu | Leu | Leu | Leu | Leu | Leu | Leu | Leu | Gly | Gly | Ala | | |
| | 30 | | | | | 35 | | | | | 40 | | | | | |
| agc | gct | cag | tac | tcc | agc | gac | ctg | tgc | agc | tgg | aag | ggg | agt | ggg | ctc | 376 |
| Ser | Ala | Gln | Tyr | Ser | Ser | Asp | Leu | Cys | Ser | Trp | Lys | Gly | Ser | Gly | Leu | |
| | 45 | | | | 50 | | | | | 55 | | | | | | |
| acc | cga | gag | gca | cgc | agc | aag | gag | gtg | gag | cag | gtg | tac | ctg | cgc | tgc | 424 |
| Thr | Arg | Glu | Ala | Arg | Ser | Lys | Glu | Val | Glu | Gln | Val | Tyr | Leu | Arg | Cys | |
| 60 | | | | 65 | | | | | 70 | | | | | 75 | | |
| tcc | gca | ggc | tct | gtg | gag | tgg | atg | tac | cca | act | ggg | gcg | ctc | att | gtt | 472 |
| Ser | Ala | Gly | Ser | Val | Glu | Trp | Met | Tyr | Pro | Thr | Gly | Ala | Leu | Ile | Val | |
| | | | 80 | | | | | 85 | | | | | 90 | | | |
| aac | cta | cgg | ccc | aac | acc | ttc | tca | cct | gcc | cag | aac | ttg | act | gtg | tgc | 520 |
| Asn | Leu | Arg | Pro | Asn | Thr | Phe | Ser | Pro | Ala | Gln | Asn | Leu | Thr | Val | Cys | |
| | 95 | | | | | 100 | | | | | 105 | | | | | |

```
                                                                           -continued
atc aag cct ttc agg gac tcc tct gga gcc aat att tat ttg gaa aaa         568
Ile Lys Pro Phe Arg Asp Ser Ser Gly Ala Asn Ile Tyr Leu Glu Lys
        110                 115                 120 act gga gaa cta aga ctg ttg gtg cgg gac atc aga ggt gag cct ggc         616
Thr Gly Glu Leu Arg Leu Leu Val Arg Asp Ile Arg Gly Glu Pro Gly
125                 130                 135 caa gtg cag tgc ttc agc ctg gag cag gga ggc tta ttt gtg gag gcg         664
Gln Val Gln Cys Phe Ser Leu Glu Gln Gly Gly Leu Phe Val Glu Ala
140                 145                 150                 155 aca ccc caa cag gac atc agc aga agg acc aca ggc ttc cag tat gag         712
Thr Pro Gln Gln Asp Ile Ser Arg Arg Thr Thr Gly Phe Gln Tyr Glu
        160                 165                 170 ctg atg agt ggg cag agg gga ctg gac ctg cac gtg ctg tct gcc ccc         760
Leu Met Ser Gly Gln Arg Gly Leu Asp Leu His Val Leu Ser Ala Pro
        175                 180                 185 tgt cgg cct tgc agt gac act gag gtc ctc ctt gcc atc tgt acc agt         808
Cys Arg Pro Cys Ser Asp Thr Glu Val Leu Leu Ala Ile Cys Thr Ser
        190                 195                 200 gac ttt gtt gtc cga ggc ttc att gag gac gtc aca cat gta cca gaa         856
Asp Phe Val Val Arg Gly Phe Ile Glu Asp Val Thr His Val Pro Glu
205                 210                 215 cag caa gtg tca gtc atc tac ctg cgg gtg aac agg ctt cac agg cag         904
Gln Gln Val Ser Val Ile Tyr Leu Arg Val Asn Arg Leu His Arg Gln
220                 225                 230                 235 aag agc agg gtc ttc cag cca gct cct gag gac agt ggc cac tgg ctg         952
Lys Ser Arg Val Phe Gln Pro Ala Pro Glu Asp Ser Gly His Trp Leu
                240                 245                 250 ggc cat gtc aca aca ctg ctg cag tgt gga gta cga cca ggg cat ggg        1000
Gly His Val Thr Thr Leu Leu Gln Cys Gly Val Arg Pro Gly His Gly
        255                 260                 265 gaa ttc ctc ttc act gga cat gtg cac ttt ggg gag gca caa ctt gga        1048
Glu Phe Leu Phe Thr Gly His Val His Phe Gly Glu Ala Gln Leu Gly
        270                 275                 280 tgt gcc cca cgc ttt agt gac ttt caa agg atg tac agg aaa gca gaa        1096
Cys Ala Pro Arg Phe Ser Asp Phe Gln Arg Met Tyr Arg Lys Ala Glu
285                 290                 295 gaa atg ggc ata aac ccc tgt gaa atc aat atg gag tga cttgcagggt         1145
Glu Met Gly Ile Asn Pro Cys Glu Ile Asn Met Glu
300                 305                 310 gacacagtac tgttgtcctt cagatgagcc atgttttgtg ggctcagtcg ctctatcata      1205
tcctgataga gattgcagac tggtggcatg ggcccagcct ggtgctagaa ctgggaaggt      1265
acatgctgct ctgaccccct taggtccagc caaggatgcc ctgacccatt ggaactgctg     1325
taaaatgcaa actaagttat tatatttttt ttgtaaaaga tgccttggtg tgccatttaa     1385
tagtgttttt acaaagttat tttcaggcat tggatttggc ctggtatatt ggtgggagct     1445
aggttatggt gtgcagtgat ggctatggct cagccttgtt attcctgtga tggaaatgta     1505
tggagcaaat actttctaat ttccccttca ttttattttc tattttaaaa gaccatcttt     1565
gccgttgaga acctttccag actgtatgga ggctgctccc attccaggga gtaaagacca     1625
ggatctgaga ctagtattac atccatctta acccatcaga tgggtacctg cattgaacct     1685
tctctgctca gctatggcct gctgtcccaa agacctttg ctctctggac agttccagat      1745
ggtgctgcct ggcttaaggg acttgttcct cccttgctcc taccaggcca ctgttgcttt     1805
ctgcatctgt cccactgaac cagtcttgtc ctttgaccct gagttttccc aaatgcacac     1865
atcaaatccc tgaataccaa gggactaacc tacttaatgg cccatttctt cagagggtgt     1925
gggttttccc tatagtaaga aaatctccac aagttgaagc ttaaacagta ggctttcgtt     1985
```

-continued

| | |
|---|---|
| catacagtcc tggaagccag aatgggtgtg agcagaatca catttcctcc ggagactcca | 2045 |
| ggagggactt tatagcttct ggtgactcca ggaatccttg gcttgtaaca atttcactct | 2105 |
| ggcattgctt tccctgccat gtgacttctg ccttgtatgt gagggcctgt atcaaatctc | 2165 |
| tgtcttggga ggatacagat cattgactta gggcccactc cggtgacctc accttcacct | 2225 |
| gaaatttact cgatttccat ttaggtcaga ggcaaaggct acaaaaaata tcaaatccgg | 2285 |
| agaaagattc aatggttagg cacttgctac tcttacaaag gacctgtgtt cgattcccat | 2345 |
| gttgggaact catgttaggt ggcttaaaat tgcctataac tacaattcca ggggatctag | 2405 |
| caacctcttc tcgccacaca caagcacaca cacacacaca cacacacaca cacaattaaa | 2465 |
| aac | 2468 |

<210> SEQ ID NO 4
<211> LENGTH: 311
<212> TYPE: PRT
<213> ORGANISM: Mus musculus

<400> SEQUENCE: 4

Met Arg Gly Ala Val Trp Ala Ala Arg Arg Ala Gly Gln Gln Trp
1               5                   10                  15

Pro Arg Ser Pro Gly Pro Gly Pro Pro Pro Pro Pro Leu
            20                  25                  30

Leu Leu Leu Leu Leu Leu Leu Leu Gly Gly Ala Ser Ala Gln Tyr Ser
            35                  40                  45

Ser Asp Leu Cys Ser Trp Lys Gly Ser Gly Leu Thr Arg Glu Ala Arg
    50                  55                  60

Ser Lys Glu Val Glu Gln Val Tyr Leu Arg Cys Ser Ala Gly Ser Val
65                  70                  75                  80

Glu Trp Met Tyr Pro Thr Gly Ala Leu Ile Val Asn Leu Arg Pro Asn
                85                  90                  95

Thr Phe Ser Pro Ala Gln Asn Leu Thr Val Cys Ile Lys Pro Phe Arg
            100                 105                 110

Asp Ser Ser Gly Ala Asn Ile Tyr Leu Glu Lys Thr Gly Glu Leu Arg
        115                 120                 125

Leu Leu Val Arg Asp Ile Arg Gly Glu Pro Gly Gln Val Gln Cys Phe
    130                 135                 140

Ser Leu Glu Gln Gly Gly Leu Phe Val Glu Ala Thr Pro Gln Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
            180                 185                 190

Asp Thr Glu Val Leu Leu Ala Ile Cys Thr Ser Asp Phe Val Val Arg
        195                 200                 205

Gly Phe Ile Glu Asp Val Thr His Val Pro Gly Gln Gln Val Ser Val
    210                 215                 220

Ile Tyr Leu Arg Val Asn Arg Leu His Arg Gln Lys Ser Arg Val Phe
225                 230                 235                 240

Gln Pro Ala Pro Glu Asp Ser Gly His Trp Leu Gly Val Thr Thr
                245                 250                 255

Leu Leu Gln Cys Gly Val Arg Pro Gly His Gly Glu Phe Leu Phe Thr
            260                 265                 270

Gly His Val His Phe Gly Glu Ala Gln Leu Gly Cys Ala Pro Arg Phe
        275                 280                 285

```
Ser Asp Phe Gln Arg Met Tyr Arg Lys Ala Glu Glu Met Gly Ile Asn
    290                 295                 300
Pro Cys Glu Ile Asn Met Glu
305                 310

<210> SEQ ID NO 5
<211> LENGTH: 1380
<212> TYPE: DNA
<213> ORGANISM: Rattus norvegicus
<220> FEATURE:
<221> NAME/KEY: misc_feature
<222> LOCATION: (1)..(1380)
<223> OTHER INFORMATION: rMTRNL cDNA
<220> FEATURE:
<221> NAME/KEY: CDS
<222> LOCATION: (197)..(1132)

<400> SEQUENCE: 5
ggcagccggc gcgcttctct ggttgcagct tgggcggctg gggcggctcc tatggtgggc      60
ggccaggggc tagacgggat ggcctgtaga cgcgcgacgt gatcagctcg cacgcggacc     120
cacgcctccc gcagcactgc ctcaacagtc tattctgtgg gtgcaggcac gcaccggtct     180
cagaccctgc cggagc atg cgg ggt gtg gtg tgg gcg gcc cgg agg cgc gcg    232
               Met Arg Gly Val Val Trp Ala Ala Arg Arg Arg Ala
                 1               5                  10 ggg cag cag tgg cct cgg tcc ccg ggc cct ggg ccg ggt ccg ccc ccg       280
Gly Gln Gln Trp Pro Arg Ser Pro Gly Pro Gly Pro Gly Pro Pro Pro
        15                  20                  25 ccg cca ccg ctg ctg ttg ctg cta ctg ctg ctg ggc ggc gcg agc          328
Pro Pro Pro Leu Leu Leu Leu Leu Leu Leu Leu Gly Gly Ala Ser
 30                  35                  40 gcg cag tac tcc agc gac ctg tgc agc tgg aag ggg agt ggg ctc acc      376
Ala Gln Tyr Ser Ser Asp Leu Cys Ser Trp Lys Gly Ser Gly Leu Thr
 45                  50                  55                  60 cgg gag gca cac agc aag gag gtg gag cag gtg tac ctg cgc tgc tca      424
Arg Glu Ala His Ser Lys Glu Val Glu Gln Val Tyr Leu Arg Cys Ser
                 65                  70                  75 gca ggc tct gtg gaa tgg atg tac cca acc ggg gcg ctc att gtt aac      472
Ala Gly Ser Val Glu Trp Met Tyr Pro Thr Gly Ala Leu Ile Val Asn
         80                  85                  90 cta cgg ccc aac acc ttc tca cct gcc cag aac ttg act gtg tgc atc      520
Leu Arg Pro Asn Thr Phe Ser Pro Ala Gln Asn Leu Thr Val Cys Ile
         95                 100                 105 aag cct ttc agg gac tcc tct ggg gcc aat att tat ttg gaa aaa act      568
Lys Pro Phe Arg Asp Ser Ser Gly Ala Asn Ile Tyr Leu Glu Lys Thr
        110                 115                 120 gga gaa cta aga ctg ttg gtg cgg gat gtc aga ggc gaa cct ggc caa      616
Gly Glu Leu Arg Leu Leu Val Arg Asp Val Arg Gly Glu Pro Gly Gln
125                 130                 135                 140 gtg cag tgc ttc agc cta gag cag gga ggc tta ttt gtg gag gcc aca      664
Val Gln Cys Phe Ser Leu Glu Gln Gly Gly Leu Phe Val Glu Ala Thr
                145                 150                 155 ccc cag cag gac atc agc aga agg acc aca ggc ttc cag tat gag ctg      712
Pro Gln Gln Asp Ile Ser Arg Arg Thr Thr Gly Phe Gln Tyr Glu Leu
        160                 165                 170 atg agt ggg cag agg gga ctg gac ctg cac gtg ctc tct gcc ccc tgt      760
Met Ser Gly Gln Arg Gly Leu Asp Leu His Val Leu Ser Ala Pro Cys
        175                 180                 185 cga cct tgc agc gac act gag gtc ctc ctt gcc atc tgc acc agt gac      808
Arg Pro Cys Ser Asp Thr Glu Val Leu Leu Ala Ile Cys Thr Ser Asp
        190                 195                 200
```

-continued

```
ttt gtt gtc cga ggc ttc atc gag gat gtc acc cat gta cca gaa cag          856
Phe Val Val Arg Gly Phe Ile Glu Asp Val Thr His Val Pro Glu Gln
205                 210                 215                 220 caa gtg tca gtc att cac cta cgg gtg agc agg ctc cac agg cag aag          904
Gln Val Ser Val Ile His Leu Arg Val Ser Arg Leu His Arg Gln Lys
            225                 230                 235 agc agg gtc ttc cag cca gct cct gag gac agt ggc cac tgg ctg ggc          952
Ser Arg Val Phe Gln Pro Ala Pro Glu Asp Ser Gly His Trp Leu Gly
240                 245                 250 cat gtc aca aca ctg ttg cag tgt gga gta cga cca ggg cat gga gaa         1000
His Val Thr Thr Leu Leu Gln Cys Gly Val Arg Pro Gly His Gly Glu
        255                 260                 265 ttc ctc ttc act gga cat gtg cac ttt ggg gag gca caa ctt gga tgt         1048
Phe Leu Phe Thr Gly His Val His Phe Gly Glu Ala Gln Leu Gly Cys
270                 275                 280 gcc cca cgc ttt agt gac ttt caa aag atg tac agg aaa gca gaa gaa         1096
Ala Pro Arg Phe Ser Asp Phe Gln Lys Met Tyr Arg Lys Ala Glu Glu
285                 290                 295                 300 agg ggc ata aac cct tgt gaa ata aat atg gag tga cttgcagggt              1142
Arg Gly Ile Asn Pro Cys Glu Ile Asn Met Glu
                    305                 310 gacaccgtac tgctgtcctt cagatgagcc atggctcagt tgctctatca aatcccgata       1202
gagattgcag actggtggca tgagccccgc ctggtgcttg aactgggaag ggaggtacat       1262
gctgctctga cccctaggt cccattcaag atgccctga cccattggaa atgttgtaaa         1322
atgcaaacta agttattata ttttttttgt aaaagaaaaa aaaaaaaaaa aaaaaaaa         1380
```

<210> SEQ ID NO 6
<211> LENGTH: 311
<212> TYPE: PRT
<213> ORGANISM: Rattus norvegicus

<400> SEQUENCE: 6

```
Met Arg Gly Val Val Trp Ala Ala Arg Arg Ala Gly Gln Gln Trp
1               5                   10                  15

Pro Arg Ser Pro Gly Pro Gly Pro Gly Pro Pro Pro Pro Pro Leu
                20                  25                  30

Leu Leu Leu Leu Leu Leu Leu Leu Gly Gly Ala Ser Ala Gln Tyr Ser
            35                  40                  45

Ser Asp Leu Cys Ser Trp Lys Gly Ser Gly Leu Thr Arg Glu Ala His
    50                  55                  60

Ser Lys Glu Val Glu Gln Val Tyr Leu Arg Cys Ser Ala Gly Ser Val
65                  70                  75                  80

Glu Trp Met Tyr Pro Thr Gly Ala Leu Ile Val Asn Leu Arg Pro Asn
                85                  90                  95

Thr Phe Ser Pro Ala Gln Asn Leu Thr Val Cys Ile Lys Pro Phe Arg
            100                 105                 110

Asp Ser Ser Gly Ala Asn Ile Tyr Leu Glu Lys Thr Gly Glu Leu Arg
        115                 120                 125

Leu Leu Val Arg Asp Val Arg Gly Glu Pro Gly Gln Val Gln Cys Phe
    130                 135                 140

Ser Leu Glu Gln Gly Gly Leu Phe Val Glu Ala Thr Pro Gln Gln Asp
145                 150                 155                 160

Ile Ser Arg Arg Thr Thr Gly Phe Gln Tyr Glu Leu Met Ser Gly Gln
                165                 170                 175

Arg Gly Leu Asp Leu His Val Leu Ser Ala Pro Cys Arg Pro Cys Ser
            180                 185                 190
```

```
Asp Thr Glu Val Leu Leu Ala Ile Cys Thr Ser Asp Phe Val Val Arg
            195                 200                 205

Gly Phe Ile Glu Asp Val Thr His Val Pro Glu Gln Gln Val Ser Val
210                 215                 220

Ile His Leu Arg Val Ser Arg Leu His Arg Gln Lys Ser Arg Val Phe
225                 230                 235                 240

Gln Pro Ala Pro Glu Asp Ser Gly His Trp Leu Gly His Val Thr Thr
            245                 250                 255

Leu Leu Gln Cys Gly Val Arg Pro Gly His Gly Glu Phe Leu Phe Thr
            260                 265                 270

Gly His Val His Phe Gly Glu Ala Gln Leu Gly Cys Ala Pro Arg Phe
            275                 280                 285

Ser Asp Phe Gln Lys Met Tyr Arg Lys Ala Glu Glu Arg Gly Ile Asn
            290                 295                 300

Pro Cys Glu Ile Asn Met Glu
305                 310

<210> SEQ ID NO 7
<211> LENGTH: 266
<212> TYPE: PRT
<213> ORGANISM: Homo sapiens
<220> FEATURE:
<221> NAME/KEY: MISC_FEATURE
<222> LOCATION: (1)..(266)
<223> OTHER INFORMATION: hMTRNL mature protein

<400> SEQUENCE: 7

Gln Tyr Ser Ser Asp Arg Cys Ser Trp Lys Gly Ser Gly Leu Thr His
1               5                   10                  15

Glu Ala His Arg Lys Glu Val Glu Gln Val Tyr Leu Arg Cys Ala Ala
            20                  25                  30

Gly Ala Val Glu Trp Met Tyr Pro Thr Gly Ala Leu Ile Val Asn Leu
            35                  40                  45

Arg Pro Asn Thr Phe Ser Pro Ala Arg His Leu Thr Val Cys Ile Arg
50                  55                  60

Ser Phe Thr Asp Ser Ser Gly Ala Asn Ile Tyr Leu Glu Lys Thr Gly
65                  70                  75                  80

Glu Leu Arg Leu Leu Val Pro Asp Gly Asp Gly Arg Pro Gly Arg Val
            85                  90                  95

Gln Cys Phe Gly Leu Glu Gln Gly Gly Leu Phe Val Glu Ala Thr Pro
            100                 105                 110

Gln Gln Asp Ile Gly Arg Arg Thr Thr Gly Phe Gln Tyr Glu Leu Val
            115                 120                 125

Arg Arg His Arg Ala Ser Asp Leu His Glu Leu Ser Ala Pro Cys Arg
130                 135                 140

Pro Cys Ser Asp Thr Glu Val Leu Leu Ala Val Cys Thr Ser Asp Phe
145                 150                 155                 160

Ala Val Arg Gly Ser Ile Gln Gln Val Thr His Glu Pro Glu Arg Gln
            165                 170                 175

Asp Ser Ala Ile His Leu Arg Val Ser Arg Leu Tyr Arg Gln Lys Ser
            180                 185                 190

Arg Val Phe Glu Pro Val Pro Glu Gly Asp Gly His Trp Gln Gly Arg
            195                 200                 205

Val Arg Thr Leu Leu Glu Cys Gly Val Arg Pro Gly His Gly Asp Phe
            210                 215                 220
```

```
Leu Phe Thr Gly His Met His Phe Gly Glu Ala Arg Leu Gly Cys Ala
225                 230                 235                 240

Pro Arg Phe Lys Asp Phe Gln Arg Met Tyr Arg Asp Ala Gln Glu Arg
                245                 250                 255

Gly Leu Asn Pro Cys Glu Val Gly Thr Asp
            260                 265

<210> SEQ ID NO 8
<211> LENGTH: 266
<212> TYPE: PRT
<213> ORGANISM: Mus musculus
<220> FEATURE:
<221> NAME/KEY: MISC_FEATURE
<222> LOCATION: (1)..(266)
<223> OTHER INFORMATION: mMTRNL mature protein

<400> SEQUENCE: 8

Gln Tyr Ser Ser Asp Leu Cys Ser Trp Lys Gly Ser Gly Leu Thr Arg
1               5                   10                  15

Glu Ala Arg Ser Lys Glu Val Glu Gln Val Tyr Leu Arg Cys Ser Ala
                20                  25                  30

Gly Ser Val Glu Trp Met Tyr Pro Thr Gly Ala Leu Ile Val Asn Leu
            35                  40                  45

Arg Pro Asn Thr Phe Ser Pro Ala Gln Asn Leu Thr Val Cys Ile Lys
        50                  55                  60

Pro Phe Arg Asp Ser Ser Gly Ala Asn Ile Tyr Leu Glu Lys Thr Gly
65                  70                  75                  80

Glu Leu Arg Leu Leu Val Arg Asp Ile Arg Gly Glu Pro Gly Gln Val
                85                  90                  95

Gln Cys Phe Ser Leu Glu Gln Gly Gly Leu Phe Val Glu Ala Thr Pro
            100                 105                 110

Gln Gln Asp Ile Ser Arg Arg Thr Thr Gly Phe Gln Tyr Glu Leu Met
        115                 120                 125

Ser Gly Gln Arg Gly Leu Asp Leu His Val Leu Ser Ala Pro Cys Arg
130                 135                 140

Pro Cys Ser Asp Thr Glu Val Leu Leu Ala Ile Cys Thr Ser Asp Phe
145                 150                 155                 160

Val Val Arg Gly Phe Ile Glu Asp Val Thr His Val Pro Glu Gln Gln
                165                 170                 175

Val Ser Val Ile Tyr Leu Arg Val Asn Arg Leu His Arg Gln Lys Ser
            180                 185                 190

Arg Val Phe Gln Pro Ala Pro Glu Asp Ser Gly His Trp Leu Gly His
        195                 200                 205

Val Thr Thr Leu Leu Gln Cys Gly Val Arg Pro Gly His Gly Glu Phe
210                 215                 220

Leu Phe Thr Gly His Val His Phe Gly Glu Ala Gln Leu Gly Cys Ala
225                 230                 235                 240

Pro Arg Phe Ser Asp Phe Gln Arg Met Tyr Arg Lys Ala Glu Glu Met
                245                 250                 255

Gly Ile Asn Pro Cys Glu Ile Asn Met Glu
            260                 265

<210> SEQ ID NO 9
<211> LENGTH: 266
<212> TYPE: PRT
<213> ORGANISM: Rattus norvegicus
```

-continued

```
<220> FEATURE:
<221> NAME/KEY: MISC_FEATURE
<222> LOCATION: (1)..(266)
<223> OTHER INFORMATION: rMTRNL mature protein

<400> SEQUENCE: 9

Gln Tyr Ser Ser Asp Leu Cys Ser Trp Lys Gly Ser Gly Leu Thr Arg
1               5                   10                  15

Glu Ala His Ser Lys Glu Val Glu Gln Val Tyr Leu Arg Cys Ser Ala
            20                  25                  30

Gly Ser Val Glu Trp Met Tyr Pro Thr Gly Ala Leu Ile Val Asn Leu
        35                  40                  45

Arg Pro Asn Thr Phe Ser Pro Ala Gln Asn Leu Thr Val Cys Ile Lys
    50                  55                  60

Pro Phe Arg Asp Ser Ser Gly Ala Asn Ile Tyr Leu Glu Lys Thr Gly
65                  70                  75                  80

Glu Leu Arg Leu Leu Val Arg Asp Val Arg Gly Glu Pro Gly Gln Val
                85                  90                  95

Gln Cys Phe Ser Leu Glu Gln Gly Gly Leu Phe Val Glu Ala Thr Pro
            100                 105                 110

Gln Gln Asp Ile Ser Arg Arg Thr Thr Gly Phe Gln Tyr Glu Leu Met
        115                 120                 125

Ser Gly Gln Arg Gly Leu Asp Leu His Val Leu Ser Ala Pro Cys Arg
130                 135                 140

Pro Cys Ser Asp Thr Glu Val Leu Leu Ala Ile Cys Thr Ser Asp Phe
145                 150                 155                 160

Val Val Arg Gly Phe Ile Glu Asp Val Thr His Val Pro Glu Gln Gln
                165                 170                 175

Val Ser Val Ile His Leu Arg Val Ser Arg Leu His Arg Gln Lys Ser
            180                 185                 190

Arg Val Phe Gln Pro Ala Pro Glu Asp Ser Gly His Trp Leu Gly His
        195                 200                 205

Val Thr Thr Leu Leu Gln Cys Gly Val Arg Pro Gly His Gly Glu Phe
    210                 215                 220

Leu Phe Thr Gly His Val His Phe Gly Glu Ala Gln Leu Gly Cys Ala
225                 230                 235                 240

Pro Arg Phe Ser Asp Phe Gln Lys Met Tyr Arg Lys Ala Glu Glu Arg
                245                 250                 255

Gly Ile Asn Pro Cys Glu Ile Asn Met Glu
            260                 265

<210> SEQ ID NO 10
<211> LENGTH: 255
<212> TYPE: PRT
<213> ORGANISM: Homo sapiens
<220> FEATURE:
<221> NAME/KEY: MISC_FEATURE
<222> LOCATION: (1)..(255)
<223> OTHER INFORMATION: hMTRNL core fragment

<400> SEQUENCE: 10

Cys Ser Trp Lys Gly Ser Gly Leu Thr His Glu Ala His Arg Lys Glu
1               5                   10                  15

Val Glu Gln Val Tyr Leu Arg Cys Ala Ala Gly Ala Val Glu Trp Met
            20                  25                  30

Tyr Pro Thr Gly Ala Leu Ile Val Asn Leu Arg Pro Asn Thr Phe Ser
        35                  40                  45
```

```
Pro Ala Arg His Leu Thr Val Cys Ile Arg Ser Phe Thr Asp Ser Ser
    50                  55                  60

Gly Ala Asn Ile Tyr Leu Glu Lys Thr Gly Glu Leu Arg Leu Leu Val
65                  70                  75                  80

Pro Asp Gly Asp Gly Arg Pro Gly Arg Val Gln Cys Phe Gly Leu Glu
                85                  90                  95

Gln Gly Gly Leu Phe Val Glu Ala Thr Pro Gln Gln Asp Ile Gly Arg
            100                 105                 110

Arg Thr Thr Gly Phe Gln Tyr Glu Leu Val Arg Arg His Arg Ala Ser
        115                 120                 125

Asp Leu His Glu Leu Ser Ala Pro Cys Arg Pro Cys Ser Asp Thr Glu
    130                 135                 140

Val Leu Leu Ala Val Cys Thr Ser Asp Phe Ala Val Arg Gly Ser Ile
145                 150                 155                 160

Gln Gln Val Thr His Glu Pro Glu Arg Gln Asp Ser Ala Ile His Leu
                165                 170                 175

Arg Val Ser Arg Leu Tyr Arg Gln Lys Ser Arg Val Phe Glu Pro Val
            180                 185                 190

Pro Glu Gly Asp Gly His Trp Gln Gly Arg Val Arg Thr Leu Leu Glu
        195                 200                 205

Cys Gly Val Arg Pro Gly His Gly Asp Phe Leu Phe Thr Gly His Met
    210                 215                 220

His Phe Gly Glu Ala Arg Leu Gly Cys Ala Pro Arg Phe Lys Asp Phe
225                 230                 235                 240

Gln Arg Met Tyr Arg Asp Ala Gln Glu Arg Gly Leu Asn Pro Cys
                245                 250                 255

<210> SEQ ID NO 11
<211> LENGTH: 255
<212> TYPE: PRT
<213> ORGANISM: Mus musculus
<220> FEATURE:
<221> NAME/KEY: MISC_FEATURE
<222> LOCATION: (1)..(255)
<223> OTHER INFORMATION: mMTRNL core fragment

<400> SEQUENCE: 11

Cys Ser Trp Lys Gly Ser Gly Leu Thr Arg Glu Ala Arg Ser Lys Glu
1               5                   10                  15

Val Glu Gln Val Tyr Leu Arg Cys Ser Ala Gly Ser Val Glu Trp Met
                20                  25                  30

Tyr Pro Thr Gly Ala Leu Ile Val Asn Leu Arg Pro Asn Thr Phe Ser
            35                  40                  45

Pro Ala Gln Asn Leu Thr Val Cys Ile Lys Pro Phe Arg Asp Ser Ser
    50                  55                  60

Gly Ala Asn Ile Tyr Leu Glu Lys Thr Gly Glu Leu Arg Leu Leu Val
65                  70                  75                  80

Arg Asp Ile Arg Gly Glu Pro Gly Gln Val Gln Cys Phe Ser Leu Glu
                85                  90                  95

Gln Gly Gly Leu Phe Val Glu Ala Thr Pro Gln Gln Asp Ile Ser Arg
            100                 105                 110

Arg Thr Thr Gly Phe Gln Tyr Glu Leu Met Ser Gly Gln Arg Gly Leu
        115                 120                 125

Asp Leu His Val Leu Ser Ala Pro Cys Arg Pro Cys Ser Asp Thr Glu
    130                 135                 140
```

```
Val Leu Leu Ala Ile Cys Thr Ser Asp Phe Val Val Arg Gly Phe Ile
145                 150                 155                 160

Glu Asp Val Thr His Val Pro Glu Gln Gln Val Ser Val Ile Tyr Leu
                165                 170                 175

Arg Val Asn Arg Leu His Arg Gln Lys Ser Arg Val Phe Gln Pro Ala
            180                 185                 190

Pro Glu Asp Ser Gly His Trp Leu Gly His Val Thr Thr Leu Leu Gln
        195                 200                 205

Cys Gly Val Arg Pro Gly His Gly Glu Phe Leu Phe Thr Gly His Val
    210                 215                 220

His Phe Gly Glu Ala Gln Leu Gly Cys Ala Pro Arg Phe Ser Asp Phe
225                 230                 235                 240

Gln Arg Met Tyr Arg Lys Ala Glu Glu Met Gly Ile Asn Pro Cys
                245                 250                 255

<210> SEQ ID NO 12
<211> LENGTH: 255
<212> TYPE: PRT
<213> ORGANISM: Rattus norvegicus
<220> FEATURE:
<221> NAME/KEY: MISC_FEATURE
<222> LOCATION: (1)..(255)
<223> OTHER INFORMATION: rMTRNL core fragment

<400> SEQUENCE: 12

Cys Ser Trp Lys Gly Ser Gly Leu Thr Arg Glu Ala His Ser Lys Glu
1               5                   10                  15

Val Glu Gln Val Tyr Leu Arg Cys Ser Ala Gly Ser Val Glu Trp Met
            20                  25                  30

Tyr Pro Thr Gly Ala Leu Ile Val Asn Leu Arg Pro Asn Thr Phe Ser
        35                  40                  45

Pro Ala Gln Asn Leu Thr Val Cys Ile Lys Pro Phe Arg Asp Ser Ser
    50                  55                  60

Gly Ala Asn Ile Tyr Leu Glu Lys Thr Gly Glu Leu Arg Leu Leu Val
65                  70                  75                  80

Arg Asp Val Arg Gly Glu Pro Gly Gln Val Gln Cys Phe Ser Leu Glu
                85                  90                  95

Gln Gly Gly Leu Phe Val Glu Ala Thr Pro Gln Asp Ile Ser Arg Arg
            100                 105                 110

Arg Thr Thr Gly Phe Gln Tyr Glu Leu Met Ser Gly Gln Arg Gly Leu
        115                 120                 125

Asp Leu His Val Leu Ser Ala Pro Cys Arg Pro Cys Ser Asp Thr Glu
    130                 135                 140

Val Leu Leu Ala Ile Cys Thr Ser Asp Phe Val Val Arg Gly Phe Ile
145                 150                 155                 160

Glu Asp Val Thr His Val Pro Glu Gln Gln Val Ser Val Ile His Leu
                165                 170                 175

Arg Val Ser Arg Leu His Arg Gln Lys Ser Arg Val Phe Gln Pro Ala
            180                 185                 190

Pro Glu Asp Ser Gly His Trp Leu Gly His Val Thr Thr Leu Leu Gln
        195                 200                 205

Cys Gly Val Arg Pro Gly His Gly Glu Phe Leu Phe Thr Gly His Val
    210                 215                 220
```

His Phe Gly Glu Ala Gln Leu Gly Cys Ala Pro Arg Phe Ser Asp Phe
225                 230                 235                 240

Gln Lys Met Tyr Arg Lys Ala Glu Glu Arg Gly Ile Asn Pro Cys
            245                 250                 255

<210> SEQ ID NO 13
<211> LENGTH: 936
<212> TYPE: DNA
<213> ORGANISM: Homo sapiens
<220> FEATURE:
<221> NAME/KEY: misc_feature
<222> LOCATION: (1)..(936)
<223> OTHER INFORMATION: hMTRNL open reading frame

<400> SEQUENCE: 13

```
atgcggggcg cggcgcgggc ggcctggggg cgcgcggggc agccgtggcc gcgaccccc       60 gccccgggcc cgccccgcc gccgctcccg ctgctgctcc tgctcctggc cgggctgctg      120
ggcggcgcgg gcgcgcagta ctccagcgac cggtgcagct ggaaggggag cgggctgacg      180
cacgaggcac acaggaagga ggtggagcag gtgtatctgc gctgtgcggc gggtgccgtg      240
gagtggatgt acccaacagg tgctctcatc gttaacctgc ggcccaacac cttctcgcct      300 gccccggcacc tgaccgtgtg catcaggtcc ttcacggact cctcggggc caatattat       360 ttggaaaaaa ctggagaact gagactgctg gtaccggacg ggacggcag gcccggccgg      420 gtgcagtgtt ttggcctgga gcagggcggc ctgttcgtgg aggccacgcc gcagcaggat      480
atcggccgga ggaccacagg cttccagtac gagctggtta ggaggcacag gcgtcggac       540 ctgcacgagc tgtctgcgcc gtgccgtccc tgcagtgaca ccgaggtgct cctagccgtc      600
tgcaccagcg acttcgccgt tcgaggctcc atccagcaag ttacccacga gcctgagcgg      660
caggactcag ccatccacct gcgcgtgagc agactctatc ggcagaaaag cagggtcttc      720
gagccggtgc ccgagggtga cggccactgg caggggcgcg tcaggacgct gctggagtgt      780
ggcgtgcggc cggggcatgg cgacttcctc ttcactggcc acatgcactt cggggaggcg      840
cggctcggct gtgccccacg cttcaaggac ttccagagga tgtacaggga tgcccaggag      900
agggggctga cccttgtga ggttggcacg gactga                                 936
```

<210> SEQ ID NO 14
<211> LENGTH: 936
<212> TYPE: DNA
<213> ORGANISM: Mus musculus
<220> FEATURE:
<221> NAME/KEY: misc_feature
<222> LOCATION: (1)..(936)
<223> OTHER INFORMATION: mMTRNL open reading frame

<400> SEQUENCE: 14

```
atgcggggtg cggtgtgggc ggcccggagg cgcgcggggc agcagtggcc tcggtccccg       60
ggccctgggc cggtccgcc cccgccgcca ccgctgctgt tgctgctact actgctgctg      120
ggcggcgcga gcgctcagta ctccagcgac ctgtgcagct ggaaggggag tgggctcacc      180
cgagaggcac gcagcaagga ggtggagcag gtgtacctgc gctgctccgc aggctctgtg      240
gagtggatgt acccaactgg ggcgctcatt gttaacctac ggcccaacac cttctcacct      300
gcccagaact tgactgtgtg catcaagcct ttcagggact cctctggagc caatatttat      360
ttggaaaaaa ctggagaact aagactgttg gtgcgggaca tcagaggtga gcctggccaa      420
gtgcagtgct tcagcctgga gcaggagggc ttatttgtgg aggcgacacc ccaacaggac      480
atcagcagaa ggaccacagg cttccagtat gagctgatga gtgggcagag gggactggac      540
```

| | |
|---|---|
| ctgcacgtgc tgtctgcccc ctgtcggcct tgcagtgaca ctgaggtcct ccttgccatc | 600 |
| tgtaccagtg actttgttgt ccgaggcttc attgaggacg tcacacatgt accagaacag | 660 |
| caagtgtcag tcatctacct gcgggtgaac aggcttcaca ggcagaagag cagggtcttc | 720 |
| cagccagctc ctgaggacag tggccactgg ctgggccatg tcacaacact gctgcagtgt | 780 |
| ggagtacgac cagggcatgg ggaattcctc ttcactggac atgtgcactt tggggaggca | 840 |
| caacttggat gtgccccacg ctttagtgac tttcaaagga tgtacaggaa agcagaagaa | 900 |
| atgggcataa accctgtga aatcaatatg gagtga | 936 |

<210> SEQ ID NO 15
<211> LENGTH: 936
<212> TYPE: DNA
<213> ORGANISM: Rattus norvegicus
<220> FEATURE:
<221> NAME/KEY: misc_feature
<222> LOCATION: (1)..(936)
<223> OTHER INFORMATION: rMTRNL open reading frame

<400> SEQUENCE: 15

| | |
|---|---|
| atgcggggtg tggtgtgggc ggcccggagg cgcgcggggc agcagtggcc tcggtccccg | 60 |
| ggccctgggc cgggtccgcc cccgccgcca ccgctgctgt tgctgctact gctgctgctg | 120 |
| ggcggcgcga gcgcgcagta ctccagcgac ctgtgcagct ggaaggggag tgggctcacc | 180 |
| cgggaggcac acagcaagga ggtggagcag gtgtacctgc gctgctcagc aggctctgtg | 240 |
| gaatggatgt acccaaccgg ggcgctcatt gttaacctac ggcccaacac cttctcacct | 300 |
| gcccagaact tgactgtgtg catcaagcct tcaggggact cctctgggc caatatttat | 360 |
| ttggaaaaaa ctggagaact aagactgttg gtgcgggatg tcagaggcga acctggccaa | 420 |
| gtgcagtgct tcagcctaga gcagggaggc ttatttgtgg aggccacacc ccagcaggac | 480 |
| atcagcagaa ggaccacagg cttccagtat gagctgatga gtgggcagag gggactggac | 540 |
| ctgcacgtgt ctctgccccc ctgtcgacct tgcagcgaca ctgaggtcct ccttgccatc | 600 |
| tgcaccagtg actttgttgt ccgaggcttc atcgaggatg tcacccatgt accagaacag | 660 |
| caagtgtcag tcattcacct acgggtgagc aggctccaca ggcagaagag cagggtcttc | 720 |
| cagccagctc ctgaggacag tggccactgg ctgggccatg tcacaacact gttgcagtgt | 780 |
| ggagtacgac cagggcatgg agaattcctc ttcactggac atgtgcactt tggggaggca | 840 |
| caacttggat gtgccccacg ctttagtgac tttcaaagaga tgtacaggaa agcagaagaa | 900 |
| agggggcataa acccttgtga ataaatatg gagtga | 936 |

<210> SEQ ID NO 16
<211> LENGTH: 801
<212> TYPE: DNA
<213> ORGANISM: Homo sapiens
<220> FEATURE:
<221> NAME/KEY: misc_feature
<222> LOCATION: (1)..(801)
<223> OTHER INFORMATION: hMTRNL mature CDS

<400> SEQUENCE: 16

| | |
|---|---|
| cagtactcca gcgaccggtg cagctggaag gggagcgggc tgacgcacga ggcacacagg | 60 |
| aaggaggtgg agcaggtgta tctgcgctgt gcggcgggtg ccgtggagtg gatgtaccca | 120 |
| acaggtgctc tcatcgttaa cctgcggccc aacaccttct cgcctgcccg gcacctgacc | 180 |
| gtgtgcatca ggtccttcac ggactcctcg ggggccaata tttatttgga aaaaactgga | 240 |
| gaactgagac tgctggtacc ggacggggac ggcaggcccg gccgggtgca gtgttttggc | 300 |

| | |
|---|---|
| ctggagcagg gcggcctgtt cgtggaggcc acgccgcagc aggatatcgg ccggaggacc | 360 |
| acaggcttcc agtacgagct ggttaggagg cacagggcgt cggacctgca cgagctgtct | 420 |
| gcgccgtgcc gtccctgcag tgacaccgag gtgctcctag ccgtctgcac cagcgacttc | 480 |
| gccgttcgag gctccatcca gcaagttacc cacgagcctg agcggcagga ctcagccatc | 540 |
| cacctgcgcg tgagcagact ctatcggcag aaaagcaggg tcttcgagcc ggtgcccgag | 600 |
| ggtgacggcc actggcaggg gcgcgtcagg acgctgctgg agtgtggcgt gcggccgggg | 660 |
| catggcgact tcctcttcac tggccacatg cacttcgggg aggcgcggct cggctgtgcc | 720 |
| ccacgcttca aggacttcca gaggatgtac agggatgccc aggagagggg gctgaaccct | 780 |
| tgtgaggttg gcacggactg a | 801 |

<210> SEQ ID NO 17
<211> LENGTH: 801
<212> TYPE: DNA
<213> ORGANISM: Mus musculus
<220> FEATURE:
<221> NAME/KEY: misc_feature
<222> LOCATION: (1)..(801)
<223> OTHER INFORMATION: mMTRNL mature CDS

<400> SEQUENCE: 17

| | |
|---|---|
| cagtactcca gcgacctgtg cagctggaag gggagtgggc tcacccgaga ggcacgcagc | 60 |
| aaggaggtgg agcaggtgta cctgcgctgc tccgcaggct ctgtggagtg gatgtaccca | 120 |
| actgggcgc tcattgttaa cctacggccc aacaccttct cacctgccca gaacttgact | 180 |
| gtgtgcatca agccttcag ggactcctct ggagccaata tttatttgga aaaaactgga | 240 |
| gaactaagac tgttggtgcg ggacatcaga ggtgagcctg gccaagtgca gtgcttcagc | 300 |
| ctggagcagg gaggcttatt tgtggaggcg acacccaac aggacatcag cagaaggacc | 360 |
| acaggcttcc agtatgagct gatgagtggg cagaggggac tggacctgca cgtgctgtct | 420 |
| gcccctgtc ggccttgcag tgacactgag gtcctccttg ccatctgtac cagtgacttt | 480 |
| gttgtccgag gcttcattga ggacgtcaca catgtaccag aacagcaagt gtcagtcatc | 540 |
| tacctgcggg tgaacaggct tcacaggcag aagagcaggg tcttccagcc agctcctgag | 600 |
| gacagtggcc actggctggg ccatgtcaca acactgctgc agtgtggagt acgaccaggg | 660 |
| catgggaat tcctcttcac tggacatgtg cactttgggg aggcacaact tggatgtgcc | 720 |
| ccacgcttta gtgactttca aggatgtac aggaaagcag aagaaatggg cataaacccc | 780 |
| tgtgaaatca atatggagtg a | 801 |

<210> SEQ ID NO 18
<211> LENGTH: 801
<212> TYPE: DNA
<213> ORGANISM: Rattus norvegicus
<220> FEATURE:
<221> NAME/KEY: misc_feature
<222> LOCATION: (1)..(801)
<223> OTHER INFORMATION: rMTRNL mature CDS

<400> SEQUENCE: 18

| | |
|---|---|
| cagtactcca gcgacctgtg cagctggaag gggagtgggc tcacccggga ggcacacagc | 60 |
| aaggaggtgg agcaggtgta cctgcgctgc tcagcaggct ctgtggaatg gatgtaccca | 120 |
| accggggcgc tcattgttaa cctacggccc aacaccttct cacctgccca gaacttgact | 180 |
| gtgtgcatca agccttcag ggactcctct ggggccaata tttatttgga aaaaactgga | 240 |
| gaactaagac tgttggtgcg ggatgtcaga ggcgaacctg gccaagtgca gtgcttcagc | 300 |

```
ctagagcagg gaggcttatt tgtggaggcc acacccagc aggacatcag cagaaggacc      360
acaggcttcc agtatgagct gatgagtggg cagaggggac tggacctgca cgtgctctct      420 gcccctgtc gaccttgcag cgacactgag gtcctccttg ccatctgcac cagtgacttt      480
gttgtccgag gcttcatcga ggatgtcacc catgtaccag aacagcaagt gtcagtcatt      540
cacctacggg tgagcaggct ccacaggcag aagagcaggg tcttccagcc agctcctgag      600
gacagtggcc actggctggg ccatgtcaca acactgttgc agtgtggagt acgaccaggg      660
catggagaat tcctcttcac tggacatgtg cactttgggg aggcacaact tggatgtgcc      720
ccacgcttta gtgactttca aaagatgtac aggaaagcag agaaggggg cataaaccct      780 tgtgaaataa atatggagtg a                                                801
```

<210> SEQ ID NO 19
<211> LENGTH: 309
<212> TYPE: PRT
<213> ORGANISM: Bos taurus
<220> FEATURE:
<221> NAME/KEY: SIGNAL
<222> LOCATION: (1)..(42)
<220> FEATURE:
<221> NAME/KEY: mat_peptide
<222> LOCATION: (43)..(309)

<400> SEQUENCE: 19

```
Met Arg Gly Ala Thr Arg Ala Ala Gly Gly Arg Ala Gly Gln Leu Trp
    -40                 -35                 -30

Pro Arg Pro Ala Pro Gly Pro Gly Pro Pro Leu Leu Leu Leu
    -25                 -20                 -15

Leu Ala Val Leu Leu Gly Gly Ala Gly Ala Gln Tyr Ser Ser Asp Leu
-10                  -5                  -1   1                   5

Cys Ser Trp Lys Gly Ser Gly Leu Thr His Glu Ala His Arg Lys Glu
                 10                  15                  20

Val Glu Gln Val Tyr Leu Arg Cys Ser Ala Gly Thr Val Glu Trp Met
             25                  30                  35

Tyr Pro Thr Gly Ala Leu Ile Val Asn Leu Arg Pro Asn Thr Phe Ser
         40                  45                  50

Pro Ser Arg Asn Leu Thr Leu Cys Ile Lys Pro Leu Arg Gly Ser Ser
55                  60                  65                  70

Gly Ala Asn Ile Tyr Leu Glu Lys Thr Gly Glu Leu Lys Leu Leu Val
                 75                  80                  85

Arg Asp Gly Asp Leu Gly Pro Gly Gln Ala Pro Cys Phe Gly Phe Glu
             90                  95                 100

Gln Gly Gly Leu Phe Val Glu Ala Thr Pro Gln Gln Asp Ile Ser Arg
         105                 110                 115

Arg Thr Thr Gly Phe Gln Tyr Glu Leu Thr Ser Arg Thr Gly Pro
         120                 125                 130

Asp Leu His Ala Leu Leu Ala Pro Cys Arg Pro Cys Ser His Thr Glu
135                 140                 145                 150

Val Leu Leu Ala Val Cys Thr Ser Asp Phe Val Val Arg Gly Ser Ile
                 155                 160                 165

Gln Lys Val Thr His Glu Pro Glu Arg Gln Glu Ser Ala Ile His Leu
             170                 175                 180

Asn Val Ser Arg Leu Tyr Arg Gln Lys Ser Arg Val Phe Arg Pro Ala
         185                 190                 195

Pro Glu Gly Glu Gly Gly Gly Trp Arg Gly Arg Val Ser Thr Leu Leu
     200                 205                 210
```

```
Glu Cys Gly Val Arg Pro Gly His Gly Glu Phe Leu Phe Thr Gly His
215                 220                 225                 230

Met His Phe Gly Glu Ala Trp Leu Gly Cys Ala Pro Arg Phe Lys Asp
                235                 240                 245

Phe Gln Arg Met Tyr Arg Asp Ala Glu Glu Arg Gly Leu Asn Pro Cys
            250                 255                 260

Glu Met Gly Thr Glu
            265

<210> SEQ ID NO 20
<211> LENGTH: 292
<212> TYPE: PRT
<213> ORGANISM: Gallus gallus
<220> FEATURE:
<221> NAME/KEY: SIGNAL
<222> LOCATION: (1)..(26)
<220> FEATURE:
<221> NAME/KEY: mat_peptide
<222> LOCATION: (27)..(292)

<400> SEQUENCE: 20

Met Arg Ser Ala Pro Ala Ala Gly Leu Leu Pro Leu Leu Gly Leu
    -25                 -20                 -15

Arg Leu Leu Leu Gly Gly Gly Ala Glu Ala Gln Tyr Ser Ser Asp Leu
-10                  -5                  -1 1                 5

Cys Asn Trp Lys Gly Ser Gly Leu Thr His Glu Ser His Lys Lys Asp
                10                  15                  20

Val Glu Gln Val Tyr Leu Arg Cys Ser Glu Gly Ser Ile Glu Trp Met
                25                  30                  35

Tyr Pro Thr Gly Ala Leu Ile Val Asn Leu Arg Pro Asn Thr Ser Pro
                40                  45                  50

Ala Ser Tyr Lys His Leu Thr Val Cys Ile Lys Pro Phe Lys Asp Ser
55                  60                  65                  70

Ala Gly Ala Asn Ile Tyr Leu Glu Lys Thr Gly Glu Leu Lys Leu Leu
                75                  80                  85

Val Arg Asp Gly Glu Arg Ser Pro Ser Lys Val Tyr Cys Phe Gly Tyr
                90                  95                  100

Asp Gln Gly Gly Leu Phe Val Glu Ala Thr Pro Gln Gln Asp Ile Ser
            105                 110                 115

Arg Lys Ile Thr Gly Phe Gln Tyr Glu Leu Met Ser Arg Gly Ile Ala
            120                 125                 130

Ser Asp Leu His Thr Val Ser Ala Pro Cys Arg Pro Cys Ser Asp Thr
135                 140                 145                 150

Glu Val Leu Leu Ala Val Cys Thr Ser Asp Phe Val Ile Arg Gly Ser
                155                 160                 165

Ile Gln Asp Val Thr Asn Glu Ala Glu Glu Gln Glu Ser Val Ile His
            170                 175                 180

Val Gly Val Asn Lys Leu Tyr Arg Gln Lys Ser Lys Val Phe Gln Leu
            185                 190                 195

Thr Gly Glu Ser Gly Asn Trp Arg Gly Gln Ile Lys Thr Leu Leu Glu
            200                 205                 210

Cys Gly Val Arg Pro Gly Asp Gly Asp Phe Leu Phe Thr Gly Arg Met
215                 220                 225                 230

His Phe Gly Glu Ala Arg Leu Gly Cys Ala Pro Arg Phe Lys Asp Phe
                235                 240                 245
```

-continued

```
Gln Arg Met Tyr Lys Glu Ala Lys Asp Lys Gly Leu Asn Pro Cys Glu
            250                 255                 260
Ile Gly Pro Asp
        265

<210> SEQ ID NO 21
<211> LENGTH: 286
<212> TYPE: PRT
<213> ORGANISM: Xenopus laevis
<220> FEATURE:
<221> NAME/KEY: SIGNAL
<222> LOCATION: (1)..(21)
<220> FEATURE:
<221> NAME/KEY: mat_peptide
<222> LOCATION: (22)..(286)

<400> SEQUENCE: 21

Met Leu Arg Arg Val Leu Leu Ser Phe Phe Met Val Ile Leu Met Asp
        -20                 -15                 -10

Arg Gly Thr Ser Gln Gln Tyr Ser Ser Asp Met Cys Asn Trp Lys Gly
 -5              -1   1               5                      10

Ser Gly Leu Thr His Glu Gly His Thr Lys Asp Val Glu Gln Val Tyr
                15                  20                  25

Leu Arg Cys Ser Glu Gly Ser Val Glu Trp Leu Tyr Pro Thr Gly Ala
             30                  35                  40

Met Ile Ile Asn Leu Arg Pro Asn Thr Leu Thr Ser Ala Tyr Lys His
         45                  50                  55

Leu Thr Val Cys Ile Lys Pro Phe Lys Asp Ser Lys Gly Ala Asn Ile
 60                  65                  70                  75

Tyr Ser Glu Lys Thr Gly Glu Leu Lys Leu Val Val Pro Asp Gly Glu
                 80                  85                  90

Asn Asn Pro His Lys Val Tyr Cys Phe Gly Leu Asp Gln Arg Gly Leu
                 95                 100                 105

Tyr Ile Glu Ala Thr Pro Gln Gln Asp Ile Ser Arg Lys Ile Thr Gly
            110                 115                 120

Phe Gln Tyr Glu Leu Ile Ser Gln Arg Thr Leu Ser Asp Leu His Thr
        125                 130                 135

Val Ser Asp Pro Cys Arg Pro Cys Ser Asp Thr Glu Val Leu Leu Ala
140                 145                 150                 155

Val Cys Ile Ser Asp Phe Val Val Lys Gly Thr Ile Gly Thr Val Thr
                160                 165                 170

Asn Asp Glu Glu Leu Gln Glu Ser Leu Ile Gly Val Thr Val Asp Lys
            175                 180                 185

Leu Tyr Arg Gln Lys Ser Lys Ile Phe Leu Pro Lys Glu Asn Gly Gly
        190                 195                 200

Trp Glu Gly Thr Ile Arg Thr Pro Arg Glu Cys Gly Val Lys Ala Gly
    205                 210                 215

Ser Gly Ser Phe Leu Phe Thr Gly Arg Met His Phe Gly Glu Pro Arg
220                 225                 230                 235

Leu Gly Cys Thr Pro Arg Tyr Ser Asp Phe Thr Arg Ile Tyr Leu Glu
                240                 245                 250

Ala Lys Lys Gln Gly Leu Asn Pro Cys Glu Ile Ser Thr Asp
            255                 260                 265

<210> SEQ ID NO 22
<211> LENGTH: 286
<212> TYPE: PRT
<213> ORGANISM: Danio rerio
```

<220> FEATURE:
<221> NAME/KEY: SIGNAL
<222> LOCATION: (1)..(21)
<220> FEATURE:
<221> NAME/KEY: mat_peptide
<222> LOCATION: (22)..(286)

<400> SEQUENCE: 22

```
Met Leu Ser Pro Phe Leu Ala Tyr Leu Leu Ser Val Val Leu Leu Cys
    -20                 -15                 -10

Arg Ile Ala Arg Ser Gln Tyr Ser Ser Asp Gln Cys Ser Trp Arg Gly
 -5              -1   1               5                  10

Ser Gly Leu Thr His Glu Gly His Thr Arg Gly Val Glu Gln Val Tyr
                 15                  20                  25

Leu Arg Cys Ala Gln Gly Phe Leu Glu Trp Leu Tyr Pro Thr Gly Ala
             30                  35                  40

Ile Ile Val Asn Leu Arg Pro Asn Thr Leu Ser Pro Ala Ala Ser Leu
         45                  50                  55

Leu Ser Val Cys Ile Lys Pro Ser Lys Glu Ser Ser Gly Thr His Ile
 60                  65                  70                  75

Tyr Leu Asp Arg Leu Gly Lys Leu Arg Leu Leu Ser Glu Gly Asp
             80                  85                  90

Gln Ala Glu Gly Lys Val His Cys Phe Asn Ile Gln Asp Gly Ala Leu
                 95                 100                 105

Phe Ile Glu Ala Val Pro Gln Arg Asp Ile Ser Arg Lys Ile Thr Ala
            110                 115                 120

Phe Gln Tyr Glu Leu Val Asn His Arg Pro Gly Ala Asp Pro Gln Ser
        125                 130                 135

Leu Ser Ala Pro Cys Gln Pro Cys Thr Asp Ala Glu Val Leu Leu Ala
140                 145                 150                 155

Val Cys Thr Ser Asp Phe Val Ala Arg Gly Arg Ile Leu Gly Val Ser
                160                 165                 170

Glu Glu Asp Glu Gln Thr Ser Val Thr Val Ser Leu Ser His Leu Tyr
            175                 180                 185

Arg Gln Lys Thr Gln Val Phe Val Ser Gly Gly Arg Ala Lys Arg
        190                 195                 200

Trp Thr Gly Phe Val Lys Met Ser Arg Gln Cys Gly Val Lys Pro Gly
    205                 210                 215

Asp Gly Glu Phe Leu Phe Thr Gly Thr Val Arg Phe Gly Glu Ala Trp
220                 225                 230                 235

Leu Ser Cys Ala Pro Arg Tyr Lys Asp Phe Leu Arg Val Tyr Gln Asp
                240                 245                 250

Ala Arg Gln Gln Gly Thr Asn Pro Cys His Leu Glu Thr Asp
            255                 260                 265
```

<210> SEQ ID NO 23
<211> LENGTH: 293
<212> TYPE: PRT
<213> ORGANISM: Homo sapiens
<220> FEATURE:
<221> NAME/KEY: SIGNAL
<222> LOCATION: (1)..(23)
<220> FEATURE:
<221> NAME/KEY: mat_peptide
<222> LOCATION: (24)..(293)

<400> SEQUENCE: 23

```
Met Gly Phe Pro Ala Ala Leu Leu Cys Ala Leu Cys Cys Gly Leu
            -20             -15                 -10

Leu Ala Pro Ala Ala Arg Ala Gly Tyr Ser Glu Glu Arg Cys Ser Trp
         -5              -1  1               5

Arg Gly Ser Gly Leu Thr Gln Glu Pro Gly Ser Val Gly Gln Leu Ala
 10              15                  20                  25

Leu Ala Cys Ala Glu Gly Ala Val Glu Trp Leu Tyr Pro Ala Gly Ala
                 30                  35                  40

Leu Arg Leu Thr Leu Gly Gly Pro Asp Pro Arg Ala Arg Pro Gly Ile
             45                  50                  55

Ala Cys Leu Arg Pro Val Arg Pro Phe Ala Gly Ala Gln Val Phe Ala
         60                  65                  70

Glu Arg Ala Gly Gly Ala Leu Glu Leu Leu Ala Glu Gly Pro Gly
     75                  80                  85

Pro Ala Gly Gly Arg Cys Val Arg Trp Gly Pro Arg Glu Arg Ala
 90                  95                 100                 105

Leu Phe Leu Gln Ala Thr Pro His Gln Asp Ile Ser Arg Arg Val Ala
                110                 115                 120

Ala Phe Arg Phe Glu Leu Arg Glu Asp Gly Arg Pro Glu Leu Pro Pro
             125                 130                 135

Gln Ala His Gly Leu Gly Val Asp Gly Ala Cys Arg Pro Cys Ser Asp
            140                 145                 150

Ala Glu Leu Leu Leu Ala Ala Cys Thr Ser Asp Phe Val Ile His Gly
        155                 160                 165

Ile Ile His Gly Val Thr His Asp Val Glu Leu Gln Glu Ser Val Ile
170             175                 180                 185

Thr Val Val Ala Ala Arg Val Leu Arg Gln Thr Pro Pro Leu Phe Gln
                190                 195                 200

Ala Gly Arg Ser Gly Asp Gln Gly Leu Thr Ser Ile Arg Thr Pro Leu
            205                 210                 215

Arg Cys Gly Val His Pro Gly Pro Gly Thr Phe Leu Phe Met Gly Trp
        220                 225                 230

Ser Arg Phe Gly Glu Ala Arg Leu Gly Cys Ala Pro Arg Phe Gln Glu
            235                 240                 245

Phe Arg Arg Ala Tyr Glu Ala Ala Arg Ala Ala His Leu His Pro Cys
250                 255                 260                 265

Glu Val Ala Leu His
                270
```

<210> SEQ ID NO 24
<211> LENGTH: 291
<212> TYPE: PRT
<213> ORGANISM: Mus musculus
<220> FEATURE:
<221> NAME/KEY: SIGNAL
<222> LOCATION: (1)..(21)
<220> FEATURE:
<221> NAME/KEY: mat_peptide
<222> LOCATION: (22)..(291)

<400> SEQUENCE: 24

```
Met Leu Val Ala Thr Leu Leu Cys Ala Leu Cys Cys Gly Leu Leu Ala
         -20             -15                 -10

Ala Ser Ala His Ala Gly Tyr Ser Glu Asp Arg Cys Ser Trp Arg Gly
     -5              -1  1               5                  10
```

Ser Gly Leu Thr Gln Glu Pro Gly Ser Val Gly Gln Leu Thr Leu Asp
            15                  20                  25

Cys Thr Glu Gly Ala Ile Glu Trp Leu Tyr Pro Ala Gly Ala Leu Arg
        30                  35                  40

Leu Thr Leu Gly Gly Pro Asp Pro Gly Thr Arg Pro Ser Ile Val Cys
    45                  50                  55

Leu Arg Pro Glu Arg Pro Phe Ala Gly Ala Gln Val Phe Ala Glu Arg
60                  65                  70                  75

Met Thr Gly Asn Leu Glu Leu Leu Ala Glu Gly Pro Asp Leu Ala
                80                  85                  90

Gly Gly Arg Cys Met Arg Trp Gly Pro Arg Glu Arg Ala Leu Phe
            95                  100                 105

Leu Gln Ala Thr Pro His Arg Asp Ile Ser Arg Arg Val Ala Ala Phe
        110                 115                 120

Arg Phe Glu Leu His Glu Asp Gln Arg Ala Glu Met Ser Pro Gln Ala
    125                 130                 135

Gln Gly Leu Gly Val Asp Gly Ala Cys Arg Pro Cys Ser Asp Ala Glu
140                 145                 150                 155

Leu Leu Leu Ala Ala Cys Thr Ser Asp Phe Val Ile His Gly Thr Ile
                160                 165                 170

His Gly Val Ala His Asp Thr Glu Leu Gln Glu Ser Val Ile Thr Val
            175                 180                 185

Val Val Ala Arg Val Ile Arg Gln Thr Leu Pro Leu Phe Lys Glu Gly
        190                 195                 200

Ser Ser Glu Gly Gln Gly Arg Ala Ser Ile Arg Thr Leu Leu Arg Cys
    205                 210                 215

Gly Val Arg Pro Gly Pro Gly Ser Phe Leu Phe Met Gly Trp Ser Arg
220                 225                 230                 235

Phe Gly Glu Ala Trp Leu Gly Cys Ala Pro Arg Phe Gln Glu Phe Ser
                240                 245                 250

Arg Val Tyr Ser Ala Ala Leu Thr Thr His Leu Asn Pro Cys Glu Met
            255                 260                 265

Ala Leu Asp
        270

<210> SEQ ID NO 25
<211> LENGTH: 291
<212> TYPE: PRT
<213> ORGANISM: Rattus norvegicus
<220> FEATURE:
<221> NAME/KEY: SIGNAL
<222> LOCATION: (1)..(21)
<220> FEATURE:
<221> NAME/KEY: mat_peptide
<222> LOCATION: (22)..(291)

<400> SEQUENCE: 25

Met Leu Val Ala Ala Leu Leu Cys Ala Leu Cys Cys Gly Leu Leu Ala
        -20                 -15                 -10

Ala Ser Ala Arg Ala Gly Tyr Ser Glu Asp Arg Cys Ser Trp Arg Gly
 -5                  -1  1                   5                  10

Ser Gly Leu Thr Gln Glu Pro Gly Ser Val Gly Gln Leu Thr Leu Asp
            15                  20                  25

Cys Thr Glu Gly Ala Ile Glu Trp Leu Tyr Pro Ala Gly Ala Leu Arg
        30                  35                  40

Leu Thr Leu Gly Gly Ser Asp Pro Gly Thr Arg Pro Ser Ile Val Cys
    45                  50                  55

```
Leu Arg Pro Thr Arg Pro Phe Ala Gly Ala Gln Val Phe Ala Glu Arg
60              65                  70                  75

Met Ala Gly Asn Leu Glu Leu Leu Leu Ala Glu Gly Gln Gly Leu Ala
            80                  85                  90

Gly Gly Arg Cys Met Arg Trp Gly Pro Arg Glu Arg Arg Ala Leu Phe
            95                  100                 105

Leu Gln Ala Thr Pro His Arg Asp Ile Ser Arg Arg Val Ala Ala Phe
        110             115                 120

Gln Phe Glu Leu His Glu Asp Gln Arg Ala Glu Met Ser Pro Gln Ala
        125             130                 135

Gln Gly Phe Gly Val Asp Gly Ala Cys Arg Pro Cys Ser Asp Ala Glu
140             145                 150                 155

Leu Leu Leu Thr Ala Cys Thr Ser Asp Phe Val Ile His Gly Thr Ile
            160                 165                 170

His Gly Val Val His Asp Met Glu Leu Gln Glu Ser Val Ile Thr Val
            175                 180                 185

Val Ala Thr Arg Val Ile Arg Gln Thr Leu Pro Leu Phe Gln Glu Gly
        190                 195                 200

Ser Ser Glu Gly Arg Gly Gln Ala Ser Val Arg Thr Leu Leu Arg Cys
    205             210                 215

Gly Val Arg Pro Gly Pro Gly Ser Phe Leu Phe Met Gly Trp Ser Arg
220             225                 230                 235

Phe Gly Glu Ala Trp Leu Gly Cys Ala Pro Arg Phe Gln Glu Phe Ser
            240                 245                 250

Arg Val Tyr Ser Ala Ala Leu Ala Ala His Leu Asn Pro Cys Glu Val
            255                 260                 265

Ala Leu Asp
        270
```